United States Patent [19]
Epstein

[11] Patent Number: 5,885,834
[45] Date of Patent: Mar. 23, 1999

[54] ANTISENSE OLIGODEOXYNUCLEOTIDE AGAINST PHOSPHODIESTERASE

[76] Inventor: Paul M. Epstein, 8 Butternut La., Weatogue, Conn. 06089

[21] Appl. No.: 940,332

[22] Filed: Sep. 30, 1997

Related U.S. Application Data

[60] Provisional application No. 60/027,207 Sep. 30, 1996.
[51] Int. Cl.$^6$ .............................. C01H 21/07; C12Q 1/68
[52] U.S. Cl. ........................... 435/375; 435/6; 435/91.31; 435/372; 536/23.1; 536/24.31; 536/24.5
[58] Field of Search .............................. 514/44; 536/24.5, 536/24.31, 23.1; 435/6, 375, 91.31, 325, 172.3, 320.1, 372

[56] References Cited

U.S. PATENT DOCUMENTS

| | | | |
|---|---|---|---|
| 4,689,320 | 8/1987 | Kaji ........................................... | 514/44 |
| 4,806,463 | 2/1989 | Goodchild et al. .......................... | 435/5 |
| 5,087,617 | 2/1992 | Smith ........................................ | 514/44 |
| 5,194,428 | 3/1993 | Agrawal et al. ............................ | 514/44 |
| 5,276,019 | 1/1994 | Cohen et al. .............................. | 514/44 |
| 5,389,527 | 2/1995 | Beavo et al. ............................. | 435/69.1 |
| 5,491,133 | 2/1996 | Walder et al. ............................. | 514/44 |
| 5,500,432 | 3/1996 | Nicolaou et al. ......................... | 514/281 |
| 5,580,771 | 12/1996 | Beavo et al. ............................. | 435/199 |
| 5,582,972 | 12/1996 | Lima et al. ................................ | 435/6 |
| 5,583,034 | 12/1996 | Green et al. .............................. | 435/6 |
| 5,599,796 | 2/1997 | Schinazi et al. .......................... | 514/44 |
| 5,602,019 | 2/1997 | Beavo et al. ............................. | 435/196 |
| 5,637,573 | 6/1997 | Agrawal et al. ........................... | 514/44 |
| 5,643,788 | 7/1997 | Baserga et al. .......................... | 435/325 |

OTHER PUBLICATIONS

Rojanasakul, Antisense oligonucleotide therapeutics: drug delivery and targeting, Advanced Drug Delivery Reviews v. 18, 115–131 (1996)Rojanasakul, Antisense oligonucleotide therapeutics: drug delivery and targeting, Advanced Drug Delivery Reviews v. 18, 1, 1996.

Gewitz et al., Facilitating olignucleotide delivery: Helping antisense deliver on its promise, PNAS 93, 3161–63 (1996).

*Primary Examiner*—John LeGuyader
*Attorney, Agent, or Firm*—Alix, Yale & Ristas, LLP

[57] ABSTRACT

Cytosolic extracts from a human lymphoblastoid B cell line, RPMI 8392, established from a patient with acute lymphocytic leukemia, contain two major forms of cyclic nucleotide phosphodiesterase (PDE): $Ca^{2+}$—calmodulin dependent PDE (PDE1) and cAMP specific PDE4 subtypes. In contrast, normal quiescent human peripheral blood lymphocytes (HPBL) are devoid of PDE1 activity. Using reverse transcription-polymerase chain reaction (RT-PCR), the mRNA encoding the 63 kDa form of PDE1 (PDE1B1) is expressed in RPMI 8392 cells, but not in normal, resting HPBL. This mRNA is, however, induced in HPBL following mitogenic stimulation by phytohemagglutinin (PHA). Also using RT-PCR, the full open reading frame for human PDE1B1 cDNA was cloned from RPMI 8392 cells and it encodes a protein of 536 amino acids with 96% identity to bovine, rat and mouse species. RT-PCR also identifies the presence of PDE1B1 in other human lymphoblastoid and leukemic cell lines. The PHA induced increase in PDE1B1, PDE4A and PDE4D mRNA is mimicked by incubation of HPBL with dibutyryl cAMP (dbcAMP) and 1-methyl-3-isobutylxanthine (IBMX). Inhibition of PDE1 or PDE4 activity by selective inhibitors induced RPMI 8392 cells, as well as the other cell lines, to undergo apoptosis. Culture of RPMI 8392 cells with an 18 nucleotide phosphorothioate antisense oligodeoxynucleotide, targeted against the translation initiation region of the RPMI 8392 mRNA, led to a specific reduction in the amount of PDE1B1 mRNA after 1 day, and its disappearance after 2 days, and induced apoptosis in these cells in a sequence specific manner. This suggests that PDEs, particularly PDE1B1 and some of the subtypes of PDE4, may be useful therapeutic targets for inducing the death of leukemic cells and for treatment of immoproliferative disorders and immune dysfunction.

9 Claims, 18 Drawing Sheets

DOSE RESPONSE (DAY 2)

TIME COURSE

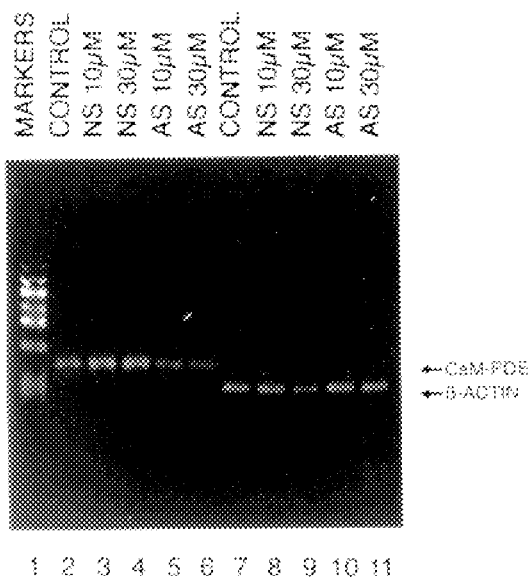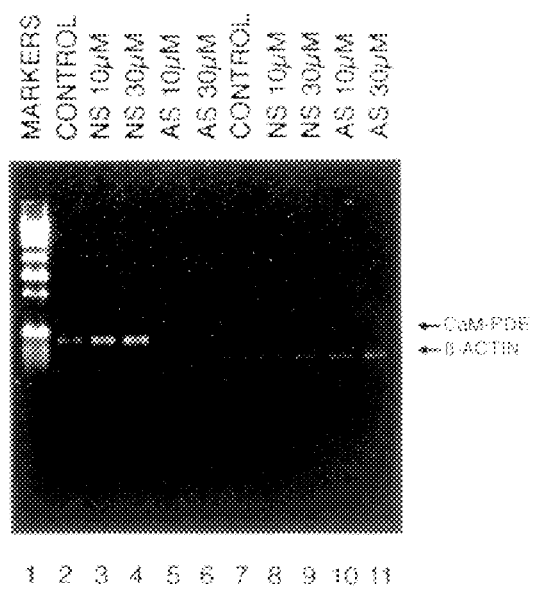
FIG.3A DAY 1
FIG.3B DAY 2

FIG. 8A

```
-34 gctrgtccmygccagccgcagaccgtggctgagc

1 ATG GAG CTG TCC CCC CGC AGT CCT AAG AAG CCG GAG ATG CTG GAG GAG TCG GAT TGC CCG TCA CCC
    CTG GAG CTG AAG TCA GCC CCC AGC AAG AAG
  1 Met Glu Leu Ser Pro Arg Ser Pro Lys Lys Pro Glu Met Leu Glu Glu Ser Asp Cys Pro Ser Pro
    Leu Glu Leu Lys Ser Ala Pro Ser Lys Lys

91 ATG TGG ATT AAG CTT CGG TCT CTG CGC TAC ATG GTG AAG CAG TTG GAG AAT GGG GAG
    ATA AAC ATT GAG GAG CTG AAG AAA AAT CTG
 31 Met Trp Ile Lys Leu Arg Ser Leu Arg Tyr Met Val Lys Gln Leu Glu Asn Gly Glu
    Ile Asn Ile Glu Glu Leu Lys Lys Asn Leu

181 GAG TAC ACA GCT TCT CTG GAA GCC GTC TAC ATA GAT GAG ACA CGG CAA ATC TTG GAC
    ACG GAG GAC CTG CAG GAG CTG CGG TCA
 61 Glu Tyr Thr Ala Ser Leu Glu Ala Val Tyr Ile Asp Glu Thr Arg Gln Ile Leu Asp
    Thr Glu Asp Leu Gln Glu Leu Arg Ser

271 GCC GTG CCT TCG GAG GTG CGG GAC TGG CTG GCC TCC ACC TTC ACC CAG CAG GCC CGG
    GCC AAA GGC CGC CGA GCA GAG GAG AAG CCC
 91 Ala Val Pro Ser Glu Val Arg Asp Trp Leu Ala Ser Thr Phe Thr Gln Gln Ala Arg
    Ala Lys Gly Arg Arg Ala Glu Glu Lys Pro

361 AAG TTC CGA AGC ATT GTG CAC GCT GTG CAG GCT GGG ATC TTC GTG GAA CGG ATG TTC CGG
    AGA ACA TAC ACC TCT GTG GGC CCC ACT TAC
121 Lys Phe Arg Ser Ile Val His Ala Val Gln Ala Gly Ile Phe Val Glu Arg Met Phe Arg
    Arg Thr Tyr Thr Ser Val Gly Pro Thr Tyr
```

FIG. 8B

```
451 TCT ACT GCG GTT CTC AAC TGT CTC AAG AAC CTG GAT CTC TGG TGC TTT GAT GTC TTT TCC
    TTG AAC CAG GCA GCA GAT GAC CAT GCC CTG
151 Ser Thr Ala Val Leu Asn Cys Leu Lys Asn Leu Asp Leu Trp Cys Phe Asp Val Phe Ser
    Leu Asn Gln Ala Ala Asp Asp His Ala Leu

541 AGG ACC ATT GTT TTT GAG TTG CTG ACT CGG CAT AAC CTC ATC AGC CGC TTC AAG ATT CCC
    ACT GTG TTT TTG ATG AGT TTC CTG GAT GCC
181 Arg Thr Ile Val Phe Glu Leu Leu Thr Arg His Asn Leu Ile Ser Arg Phe Lys Ile Pro
    Thr Val Phe Leu Met Ser Phe Leu Asp Ala

631 TTG GAG ACA GGC TAT GGG AAG TAC AAG AAT CCT TAC CAC AAC CAG ATC CAC GCA GCC GAT
    GTT ACC CAG ACA GTC CAT GAG CAC ACG GGC ACT
211 Leu Glu Thr Gly Tyr Gly Lys Tyr Lys Asn Pro Tyr His Asn Gln Ile His Ala Ala Asp
    Val Thr Gln Thr Val His Cys Phe Leu Leu

721 CGC ACA GGG ATG GTG CAC TGC CTG TCG GAG ATT GAG CTC CTG GCC ATC ATC TTT GCT GCA
    GCT ATC CAT GAT TAT GAG CAC ACG GGC ACT
241 Arg Thr Gly Met Val His Cys Leu Ser Glu Ile Glu Leu Leu Ala Ile Ile Phe Ala Ala
    Ala Ile His Asp Tyr Glu His Thr Gly Thr

811 ACC AAC AGC TTC CAC ATC CAG ACC AAG TCA GAA TGT GCC ATC GTG TAC AAT GAT CGT TCA
    GTG CTG GAG AAT CAC CAC ATC AGC TCT GTT
271 Thr Asn Ser Phe His Ile Gln Thr Lys Ser Glu Cys Ala Ile Val Tyr Asn Asp Arg Ser
    Val Leu Glu Asn His His Ile Ser Ser Val
```

FIG. 8C

```
901 TTC CGA TTG ATG CAG GAT GAT GAG ATG AAC ATT TTC ATC AAC CTC ACC AAG GAT GAG TTT
    Phe Arg Leu Met Gln Asp Asp Glu Met Asn Ile Phe Ile Asn Leu Thr Lys Asp Glu Phe
    GTA GAA CTC CGA GCC CTG GTC ATT GAG ATG
    Val Glu Leu Arg Ala Leu Val Ile Glu Met

991 GTG TTG GCC ACA GAC ATG TCC TGC CAT TTC CAG CAA GTG AAG ACC ATG AAG ACA GCC TTG
    Val Leu Ala Thr Asp Met Ser Cys His Phe Gln Gln Val Lys Thr Met Lys Thr Ala Leu
    CAA CAG CTG GAG AGG ATT GAC AAG CCC AAG
    Gln Gln Leu Glu Arg Ile Asp Lys Pro Lys

1081 GCC CTG TCT CTA CTG CTC CAT GCT GAC ATC AGC CAC CCA ACC AAG CAG TGG TTG GTC
     Ala Leu Ser Leu Leu Leu His Ala Asp Ile Ser His Pro Thr Lys Gln Trp Leu Val
     CAC AGC CGT TGG ACC CTC AAG GCC CTC ATG GAG
     His Ser Arg Trp Thr Leu Lys Ala Leu Met Glu

1171 GAA TTC TTC CGT CAG GGT GAC AAG GAG GCA GAG TTG GGC CTG CCC TTT TCT CCA CTC TGT
     Glu Phe Phe Arg Gln Gly Asp Lys Glu Ala Glu Leu Gly Leu Pro Phe Ser Pro Leu Cys
     GAC CGC ACT TCC ACT CTA GTG GCA CAG TCT
     Asp Arg Thr Ser Thr Leu Val Ala Gln Ser

1261 CAG ATA GGG TTC ATC GAC TTC ATT GTG GAG CCC ACA TTC TCT GTG CTG ACT GAC GTG GCA
     Gln Ile Gly Phe Ile Asp Phe Ile Val Glu Pro Thr Phe Ser Val Leu Thr Asp Val Ala
     GAG AAG AGT GTT CAG CCC CTG GCG GAT GAG
     Glu Lys Ser Val Gln Pro Leu Ala Asp Glu

1351 GAC TCC AAG TCT AAA AAC CAG CCC AGC TTT CAG TGG CGC CAG CCC TCT CTG GAT GTG GAA
     Asp Ser Lys Ser Lys Asn Gln Pro Ser Phe Gln Trp Arg Gln Pro Ser Leu Asp Val Glu
     GTG GGA GAC CCC AAC CCT GAT GTC AGC
     Val Gly Asp Pro Asn Pro Asp Val Ser
```

FIG. 8D

```
1441 TTT CGT TCC ACC TGG GTC AAG CGC ATT CAG GAG AAC AAG CAG AAA TGG AAG GAA CGG GCA
     GCA AGT GGC ATC ACC AAC CAG ATG TCC ATT
 481 Phe Arg Ser Thr Trp Val Lys Arg Ile Gln Glu Asn Lys Gln Lys Trp Lys Glu Arg Ala
     Ala Ser Gly Ile Thr Asn Gln Met Ser Ile

1531 GAC GAG CTG TCC CCC TGT GAA GAA GAG GCC CCC CCA TCC GCC GAA GAT GAA CAC AAC
     CAG AAT GGG AAT CTG GAT TAG ccctgggctg
 511 Asp Glu Leu Ser Pro Cys Glu Glu Glu Ala Pro Pro Ser Pro Ala Glu Asp Glu His Asn
     Gln Asn Gly Asn Leu Asp *

1623 gcccagtgtcttcattgagtcgtccaaagtgtttgatgtcatcagcaccatccatcaggactgctcccccatctgctccaag
     ggagcgtggtcgtggaagaaacaaccacctgaaggccaa
1742 atgccagagatttggggtggggaaaggccccctcccacctgacaccactgggtgcacttaatgttccggcagca
     agactgggaacttcaggctccagtgtcactgtgccca
1871 tccctcagcctctgattctcttcatgccaggtggctgccaggaggcgggagcttcctgaggcttcccaggccctt
     ggggaagggtcagagatgccagcccctgggaccctcccc
1980 atcctttgcctccaagttttctaagcaatacattttggggttcctcagcccccaccccagatcttagctgcagg
     tctgggtgcccctttcctccctgggaaggctgggaata
2099 ggatagaaagctgggggtttcagagccctatgtgtgggaggggagtgattcctccaggcatggtaccttttctagg
     atctgggaatggggtggagaggacatctcttcacccag
2218 aattgcgggaattc
```

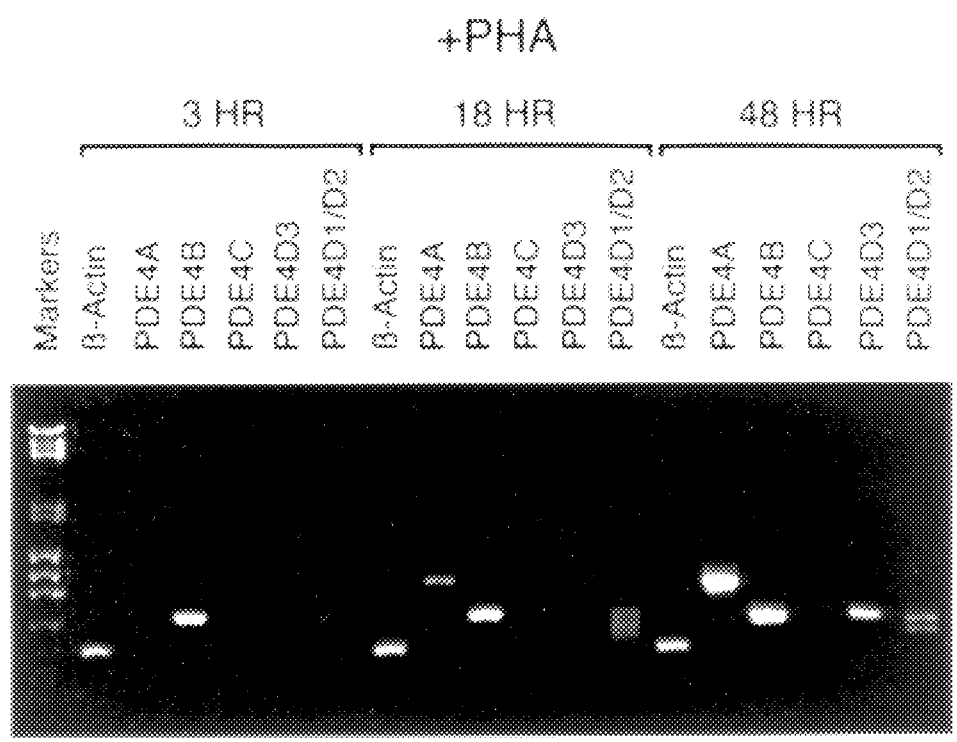

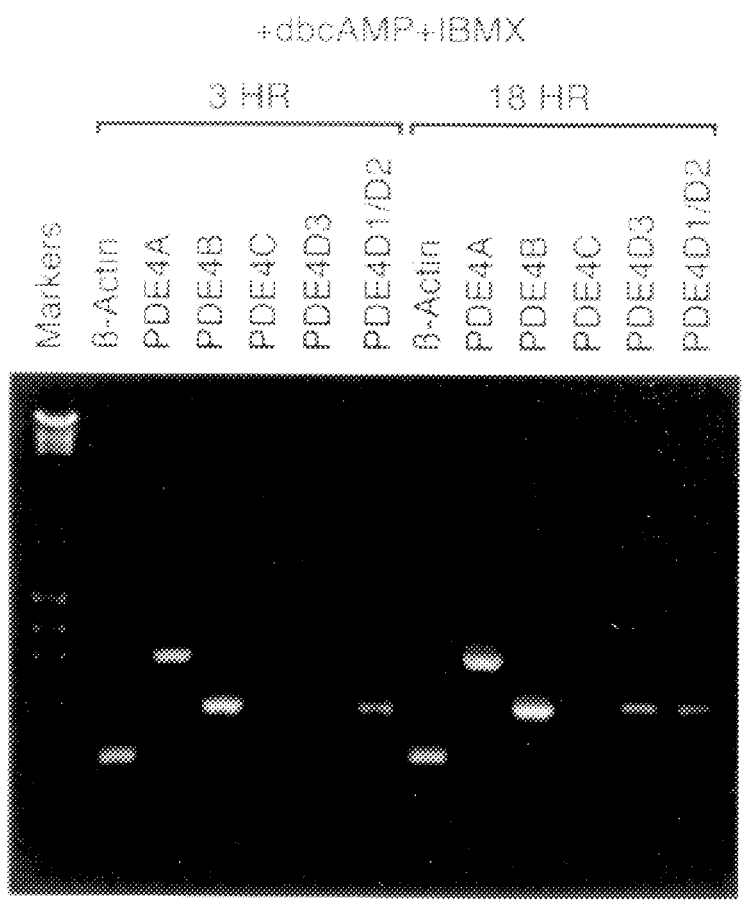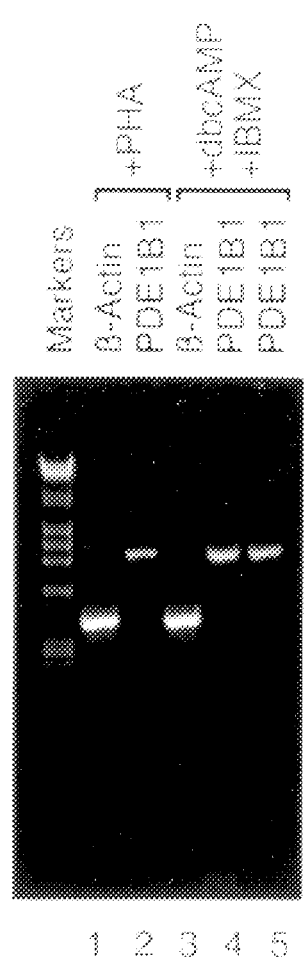

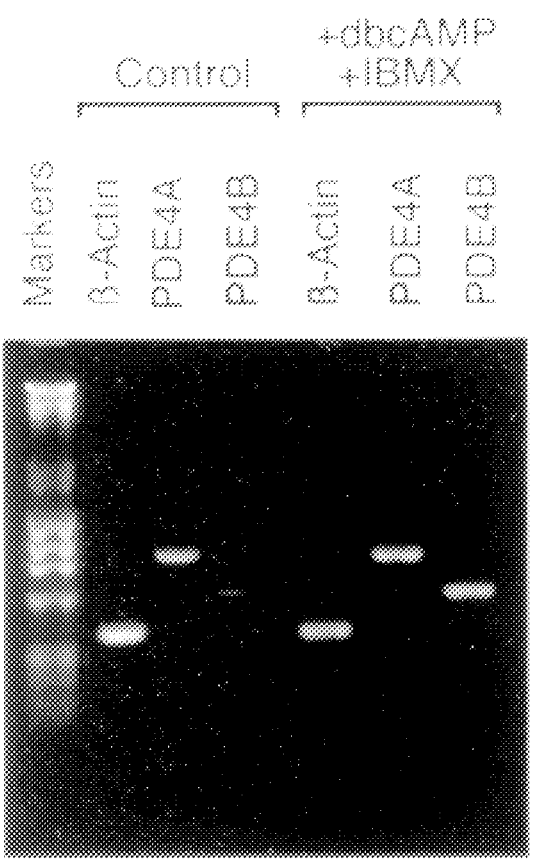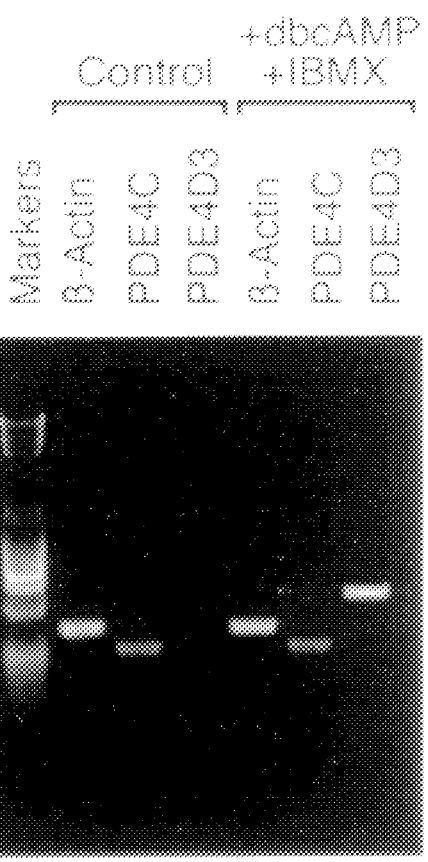

ANTISENSE OLIGODEOXYNUCLEOTIDE AGAINST PHOSPHODIESTERASE

This application claims the benefit of U.S. Provisional application Ser. No. 60/027,207, filed Sep. 30, 1996.

FIELD OF THE INVENTION

The present invention relates generally to phosphodiesterase (PDE) and is more particularly directed to the cloning and sequencing of the cDNA for a gene family of PDE as well as the synthesis of a selective PDE inhibitor targeted against this gene and the inducement of programmed cell death or apoptosis by the disruption of the expression of the gene.

BACKGROUND OF THE INVENTION

In many cell lines, cyclic adenosine monophosphate, cAMP, is known to have a regulatory effect on cell proliferation and cell function. Early studies by Tomkins and colleagues as reported in *Proc. Natl. Acad. Sci.* USA, Vol. 70, pp. 76–79 (1973) and *Am. J. Pathol.* Vol. 81, pp. 199–204 (1975), have shown that, using an S49 mouse lymphoma cell line, cAMP induces these cells to undergo reversible G1 arrest, followed by cytolysis. Mutants resistant to cAMP-induced death were deficient in cAMP-dependent protein kinase, indicating that this enzyme functions in cAMP-induced cytolysis. More recent studies culminating with Lomo et al, *J. ImmunoL*, Vol. 154, pp. 1634–1643 (1995), have shown that the death induced by cAMP is apoptotic cell death, and occurs in normal as well as transformed lymphoid cells.

Since the first report in 1958 of an enzymatic activity capable of hydrolyzing cAMP, it has become clear that this enzymatic activity, termed cyclic nucleotide phosphodiesterase (PDE), consists of a complex isozymic superfamily represented by different forms, of which more than thirty have been identified and cloned. These isozymic PDE forms have been grouped into seven broad gene families based upon similar structural and functional relationships: $Ca^{2+}$—calmodulin-dependent (PDE1), cyclic guanosine monophosphate, cGMP, stimulated (PDE2), cGMP inhibited (PDE3), cAMP specific (PDE4), cGMP specific (PDE5), photoreceptor (PDE6), and higher affinity drug-resistant cAMP specific (PDE7). A number of reviews have been written that describe the characteristics of these different PDE forms, their regulation, potential physiological function, and progress in development of pharmacological inhibitors of PDE as therapeutic agents. Gene family-specific inhibitors have been found for all but the PDE7 gene family, but no pharmacological inhibitor is yet capable of selectively inhibiting a specific PDE isoform within a given gene family. It is believed that selective elevation of cAMP levels in transformed lymphocytes could provide a means to selectively induce apoptosis in these cells. One means of elevating cAMP levels in cells is through the inhibition of cyclic nucleotide phosphodiesterase (PDE) activity. Early studies showed that PDE activity is greatly increased in actively growing and transformed lymphocytes, that PDE activity is induced in human peripheral blood lymphocytes (HPBL) following mitogenic stimulation, and that PDE inhibitors profoundly inhibit mitogenic stimulation of HPBL. Thus, while increased PDE activity is shown in growing, cultured lymphoblastoid and leukemic cells, relative to normal, resting HPBL and long term induction of PDE activity is shown to occur in HPBL following mitogenic stimulation, the specific PDE isozyme(s) induced in HBPL were not fully characterized. Initial characterizations of PDE in HPBL suggested it was comprised mainly of PDE4 activity, and recent cloning analysis shows expression of PDE4 mRNA in HPBL. More recent biochemical analysis of PDE in purified human T lymphocytes using ion exchange HPLC separation and in HPBL by sensitivity to selective PDE inhibitors gives evidence for the presence in these cells of PDE3 as well as PDE4. The presence of PDE1 activity in a human B lymphoblastoid cell line isolated from a patient with acute lymphocytic leukemia has been documented, and it has been shown that PDE 1 activity is absent in normal, resting HPBL. Using bovine peripheral blood lymphocytes, PBL, investigators have confirmed an absence of PDE 1 activity in resting PBL and showed its appearance in these cells following mitogenic stimulation. Characterization with monoclonal antibodies suggested that the induced PDE1 activity in bovine PBL belongs to the PDE1B, 63kDa $Ca^{2+}$—calmodulin-dependent PDE, gene family.

The cDNA for PDE1B1 has been cloned from bovine, rat and mouse brain cDNA libraries. The expression of the mRNA for PDE1B1 in different tissues as assessed by Northern analysis has shown it to be restricted largely to the brain, where it is enriched in the striatum. In brain, PDE1B1 mRNA is expressed as a single species of ~3–4 kb, whereas in mouse S49 cells three transcripts are seen at 4.4, 7, and 12 kb.

In addition to the many negative regulatory effects of cAMP, there is evidence that cAMP may play a biphasic role, being both a positive and negative regulator of lymphocyte proliferation since both mouse and human lymphocytes exhibit a late (10–50 hr.) surge in intracellular cAMP concentration following stimulation of proliferation by mitogens, which decreases just prior to the onset of DNA synthesis. Interruption of either the increase of this cAMP surge or prevention of its decrease, leading to sustained elevated cAMP, prevents the commencement of DNA synthesis.

Since sustained elevations of cAMP prevent DNA synthesis, for proliferation to proceed it is necessary for the stimulated lymphocyte to decrease its cAMP levels, and one mechanism by which it may do this is through the activation of PDE activity. Indeed, a late induction of PDE activity following mitogenesis has been described, and PDE inhibitors have been shown to profoundly inhibit lymphocyte mitogenesis.

It is also known that the proliferation of breast and prostate cancer cells is inhibited by cAMP, giving promise to the possibility that cAMP analogs or agents that raise intracellular levels of cAMP might be used in the treatment of those cancers. However, due to adverse side effects and the absence of selectivity progress has been slow, cAMP has profound effects on the metabolic machinery, growth regulatory properties and regulation of gene transcription in most cells of the body. Indiscriminate application or elevation of cAMP throughout would be likely to produce a whole array of effects, some of which may be highly undesirable. The goal, then, for employing cAMP therapy in cancer treatment is to come up with a way to selectively raise cAMP levels in cancer tissue.

The level of cAMP in cells is controlled by its rate of synthesis by adenylyl cyclase (AC) and its rate of degradation by cyclic nucleotide phosphodiesterases (PDEs). cAMP can readily be increased by agents in cancer cells by agents acting through stimulation of AC, such as catecholamines or prostaglandins acting through receptors coupled to AC, cholera toxin acting on Gs, or forskolin directly stimulating the AC catalytic unit, but none of these treatments is selective. If a specific form(s) of PDE can be shown to predominate in cancer cells, and not elsewhere, then selective inhibition of the PDE form should increase cAMP in cancer cells primarily, if not exclusively, and thereby avoid the adverse effects associated with earlier attempts at cAMP therapy.

SUMMARY OF THE INVENTION

The present invention relates to the synthesis of selective PDE inhibitors specific to forms of PDE predominating in particular cell lines and the inducement of terminal cell differentiation or programmed cell death (apoptosis) using an antisense oligodeoxynucleotide system or approach. This necessitates the identification of the most abundant isoforms of the targeted cell's PDE gene family and the cloning and sequencing of the cDNAs that exhibit the highest levels of expression. The invention includes the development of phosphorothioate antisense oligodeoxynucleotides (AS ODNs) targeted to disrupt the expression of the specific cell lines.

Since cAMP is involved in regulation of almost all fundamental cellular processes, such as hormonal responsiveness, neurotransmission, glycogen and lipid metabolism, cell growth, apoptosis, and gene regulation, targeting antisense oligonucleotides or oligodeoxynucleotides, AS ODNs, to specific forms of PDE can inhibit that isotype and alter cAMP levels in specific tissues, cells, or cellular compartments, and therefore can be used in the treatment of virtually any type of human disease. The approach of developing ODNs targeted to a specific form of PDE expressed selectively in leukemic cells, and the demonstration that it selectively kills these cells, and therefore holds great promise in the treatment of leukemia, is only one example of how this approach can work. The same approach can be employed for cAMP controlled cancer cell lines, either alone or in conjunction with cAMP level stimulants or chemical agents that have been shown to exert an antiproliferation effect on carcinoma cell lines.

The present invention entails several parts: 1) cloning and sequencing of the complete open reading frame (ORF) of the cDNA for the 63 kDa calmodulin-dependent phosphodiesterase (PDE1B1) from a cultured lymphoblastoid cell line established from a patient with acute lymphocytic leukemia, 2) synthesis of an 18 nucleotide (nt) phosphorothioate antisense oligodeoxynucleotide (PS ODN) targeted against the translation initiation region of this gene, and 3) demonstration that the disruption of the expression of this gene by this AS ODN leads to apoptosis (programmed cell death) of cultured human leukemic cells, in a sequence specific manner.

The PDE4 family is composed of four distinct but homologous genes, designated A–D. In addition to the induction of the PDE1 activity following mitogenic stimulation by phytohemagglutinin (PHA) or folowing incubation of the cells with dibutyryl cAMP (dbcAMP) and 1-methyl-3-isobutylxanthine (IBMX), it has been found that there is an induction of the expression of the PDE4A and D genes following mitogenic stimulation of HPBL. Incubation of HPBL with cell permeable cAMP analogs and PDE inhibitors mimics this same induction, suggesting that this induction may be secondary to the surge of cAMP that precedes DNA synthesis, following mitogen stimulation. Isolated, quiescent HPBL express mRNA for PDE4B as the principal transcript. Hence, in addition to the PDE1B1 gene, selective members of the PDE4 gene family also are good targets for modulation of inflammatory and immunoproliferative disorders and immune dysfunction.

Additionally, it is known that proliferation of carcinomas such as breast and prostate cancer cells is inhibited by cAMP. However, without selectivity adverse side effects can occur. Accordingly, through the use of antisense technology, selective inhibition of the expression of cell-specific PDE isoforms can be achieved, thus providing a means for examining the physiological function of these specific PDE isozymes. Such selective and specific targeting could permit cell differentiation or apoptosis of these cells with little or no effect on normal breast or prostate tissue.

The present invention includes the sequence of the full open reading frame, ORF, of the human form of PDE1B1, obtained by reverse transcription-polymerase chain reaction (RT-PCR) from a human lymphoblastoid cell line, demonstrates the expression of the mRNA for PDE1B1 in several lymphoblastoid and leukemic cell lines, as well as in mitogen-stimulated HPBL, and shows that inhibition of PDE1B1 induces apoptosis of these cells.

According to the present invention, it has been found that several types of lymphoblastoid and leukemic cells of T and B cell origin express the gene for the 63 kDa calmodulin-dependent PDE (PDE1B1). Isolated HPBL do not express this gene, but are induced to do so following mitogenic stimulation. An induction of PDE1 has also been observed in Chinese hamster ovary cells, following treatment with phorbol ester. Using RT-PCR, the cDNA representing the full ORF for PDE1B1 from RPMI 8392 cells was cloned and sequenced, and based on this sequence, AS ODN of PDE1B1 was synthesized.

Blockage or inhibition of PDE activity by the selective PDE1 inhibitor or blockage of the expression of the gene for PDE1B1 by treatment with AS ODN led to apoptosis of these cells. RPMI 8392 cells, which also contain PDE4 and PDE1 may both serve to regulate a common pool for cAMP in these cells. The same is true for the actions of PDE3 and PDE4 in human lymphocytes, based on their synergistic effects on inhibition of lymphocyte proliferation.

Use of AS ODNs to block the expression of specific genes involved in growth regulation of lymphoid cells is of particular interest as a result of the potential for such an approach to provide a novel therapeutic strategy for treatment of leukemias. With the exception of anti-bcr-abl AS ODN, which can be targeted to a leukemia-specific sequence in CML cells resulting from a chromosomal translocation, all the other AS ODNs used in this manner have the capability to block normal cellular functions, since the targeted genes are also expressed in normal cells as well.

The approach of using anti-PDE AS ODN to induce apoptosis of leukemic cells, as demonstrated in accordance with this invention, has the potential to be selective for leukemic cells. Although PDE4 could be used as a therapeutic target, PDE4 is clearly present in normal, resting HPBL and has a widespread distribution in tissues throughout the human body. Similarly, analysis of tissue distribution of PDE7 show it to be fairly widespread and to predominate in skeletal muscle. The present invention concentrates, therefore, on PDE1B1 as a target, since the mRNA for PDE1B1 is selectively expressed in leukemic and actively growing lymphocytes, and not in resting HPBL. Moreover, the expression of PDE1B1 in tissues other than activated or transformed lymphocytes is largely restricted to areas of the brain. Since phosphorothioate AS ODNs distribute very poorly into the brain, brain function should be little affected by therapeutic AS ODNs targeted to leukemic forms of PDE1B1. A few other tissues express small amounts of PDE1B, either as alternate spliced forms (kidney papilla) or multiple transcripts (testes, thymus) of the mRNA. Hence, very selective AS ODNs targeted specifically to PDE1B1 in leukemic cells can be produced, especially if polymorphism or variants of PDE1B can be demonstrated in these cells.

It has also been found that in addition to the induction of mRNA for PDE1B1, an induction of mRNA for some subtypes of the high affinity, cAMP specific PDE4 gene family occurs as well; specifically PDE4A and PDE4D. Since the same pattern of induction is mimicked by incubation of HPBL with dibutyryl cAMP (dbcAMP) and IBMX, and since the time course for the PHA induction of the PDE mRNAs follows that of the reported PHA-induced elevation of cAMP and activation of cAMP response element binding, CREB, proteins in lymphocytes, it suggests that the induction of PDE mRNA in HPBL is mediated by cAMP.

cAMP-mediated induction of PDE has been known for a long time, and in most of these cases, where examined, the induced activity was representative of high affinity, cAMP specific, PDE4 activity. In the present invention, it is found that not only does cAMP induce the mRNA for PDE4, but it induces the mRNA for PDE1B1 as well. Since PDE1 appears to be induced by agents that activate both protein kinase A, PKA, and protein kinase C, PKC, pathways, it suggests that the promoter region that regulates the transcription of PDE1 mRNA is under control of both the PKA and PKC signaling pathways. Consistent with this is the observation that the CREB protein which, following its activation by phosphorylation, binds to cAMP response element, CRE, regions of DNA to activate transcription, can be phosphorylated and activated on the same serine residue by both PKA and PKC.

According to the present invention, it is shown that sequence-specific disruption of the gene for PDE1B1 by AS ODN and for different PDE4 subtypes by specific pharmacological inhibitors of PDE4 induces apoptosis in human leukemic cells, therefore providing potential promise and a basis for development of novel therapeutic strategies for the treatment of leukemia.

BRIEF DESCRIPTION OF THE DRAWINGS

In the drawings

FIG. 3 is a pair of photographs showing the effect of antisense to PDE1B1 on the expression of β-actin and PDE1B1 mRNA at different time spans;

FIG. 8 is the nucleotide and amino acid sequences SEQ. ID NOS:1 and 2, respectively, of the open reading frame (ORF) of human RPMI-8392 cell PDE1B1;

FIGS. 11A–11C are a series of photographs of gels showing RT-PCR amplification of transcripts for PDE1B1 and different PDE4 subtypes in quiescent and mitogen-stimulated HPBL.

FIGS. 12A and 12B are photographs of gels showing the effect of dbcAMP and IBMX on transcripts for PDE1B1 and different PDE4 subtypes in HPBL as determined by RT-PCR amplification.

FIGS. 14A and 14B are photographs of gels showing RT-PCR amplification of transcripts for different PDE 4 subtypes in RPMI 8392 cells.

DESCRIPTION OF A PREFERRED EMBODIMENT

Figure 1:
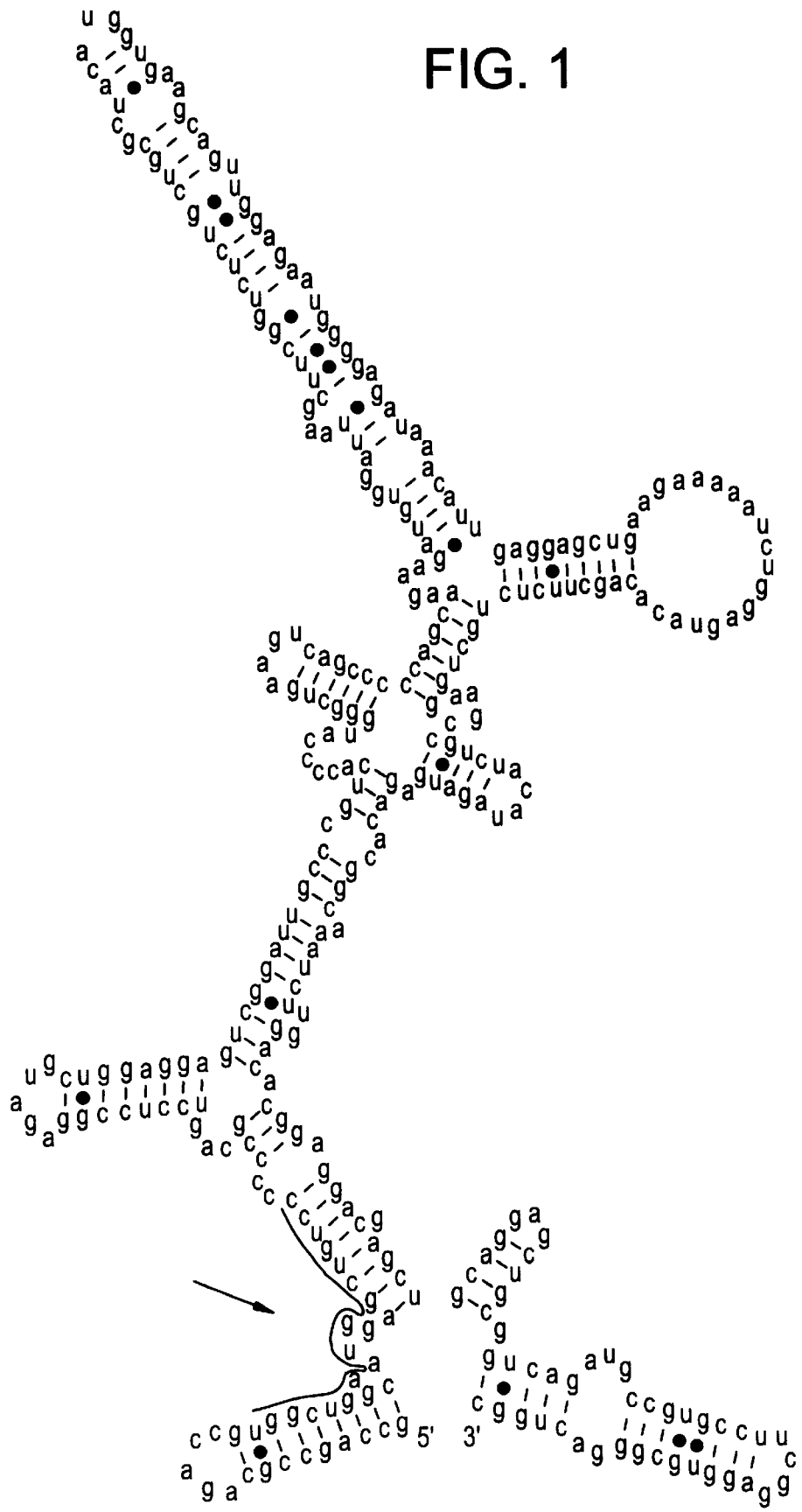
FIG. 1 is a computer program predicted secondary structure SEQ. ID NO:3, of the 5' end of the PDE1B1 mRNA.

Using antisense technology, it is possible to develop small oligonucleotides or oligodeoxynucleotides (ODNs), plasmids, or retroviral vectors that can be introduced easily into viable cells in order to inhibit gene products specifically. In designing antisense ODNs (AS ODNs) for use in biological systems, it is necessary to take into account several factors, including i) optimum length of the ODN for maximum effectiveness and sequence specificity, ii) region of mRNA to be targeted, iii) ability of ODN to get into cells, iv) protection of ODN from degradation by nucleases, and v) potential non-sequence specific effects of the ODNs. The specificity of AS ODNs results from the highly specific hybridization to their complementary target sequence on the mRNA, which causes inhibition of protein expression by at least two now widely accepted mechanisms. The first is degradation of RNA by the ubiquitous enzyme, RNase H, which selectively cleaves the RNA of DNA-RNA heteroduplexes, and the second is the arrest of translation initiation caused by AS ODN hybridization to the 5'-untranslated region or the translation initiation site on the mRNA. Additional ways in which AS ODNs may act could include defective splicing due to steric interference by the ODNs bound to the RNAs, specific blockage of mRNA transport, or interference with 5' capping or polyadenylation of the RNA.

Unmodified phosphodiester backbone ODNs (PO ODNs) bound to mRNA trigger RNase H activity, which, as mentioned, can be one of the principle ways in which AS ODNs work. Of hundreds of chemically modified derivatives of ODNs that have been made, the only type in addition to PO ODNs that have retained the ability to trigger RNase H activity are the phosphorothioates. Phosphorothioate ODNs (PS ODNs) are analogs in which one of the non-bridging oxygens in the phosphodiester group is substituted with sulfur at each interbase phosphate atom. In addition to their ability to trigger degradation of the target mRNA, the sulfur group substitution in PS ODNs confers upon them nuclease resistance, which is a significant advantage over PO ODNs, which are readily broken down by nucleases, primarily 3'-exonucleases, in serum and in cells. Hence, the majority of AS ODN studies to date have employed PS ODNs, and all of the first generation AS ODNs in clinical trials are PS ODNs. Both PO and PS ODNs can readily be custom synthesized and ordered from commercial companies specializing in DNA synthesis. Regardless of the source of the ODN synthesis, for reproducibility, it is recommended that the ODNs be highly purified and that details and proof of their purity be supplied by the company synthesizing them. Despite their nuclease resistance and retention of RNase H activation, PS ODNs are not without drawbacks.

As a result of their polyanionic nature and sulfur modification, PS ODNs have been found to bind to a variety of proteins with 10–100 fold greater affinity than corresponding PO ODNs, leading to nonspecific effects. Moreover, the Tm of a PS ODN for RNA is about 0.5° C. less per nucleotide than for a corresponding PO ODN, and hence the PS ODNs have somewhat reduced affinity for RNA. As a result of these drawbacks, a wide variety of chemical modifications have been introduced into ODNs, in an effort to improve upon their specificity and efficacy. These modifications have included methylphosphonates, phosphoramidates, phosphorodithioates, N3'→P5'-phosphoramidate and PS oligoribonucleotides and their 2'-O-alkyl derivatives, among others. These various ODN analogs differ with respect to their affinity for RNA, stability to nucleases, and extent to which they activate RNase H. An N3'→P5'-phosphoramidate AS ODN to c-myc was recently shown to be more effective in vivo than its PS ODN counterpart in enhancing survival in a mouse model of leukemia. Of particular interest are chimeric or mixed-backbone ODNs that retain only some of the bases as the PS type, either in the middle, or at the ends of the ODN, in conjunction with other modifications, which reduce their nonspecific effects, yet retain enough of the PS ODN structure to still activate RNase H activity. GEM 132, a second generation 20-mer AS ODN of this type is made by Hybridon Inc. of Worcester, Mass. Other chimeric ODNs are marketed commercially by Oligos Etc. of Wilsonville, Oreg.

The length of the ODN can affect whether the targeted RNA is inhibited specifically, or whether the ODN binds to other, unintended RNAs, and inhibits them nonspecifically, as well. Based on a size estimate of ≈3×10⁹ base pairs (nt) for the human genome, it can be calculated that a sequence of 17 nucleotides (nt) should occur only once. Since only about 1% of the genome is estimated to code for genes, and only about 10% of these genes are expressed in a given tissue, an AS ODN targeted to a specific mRNA should be able to be made shorter than this without losing its specificity. Indeed, sequence specific inhibition of the expression of cloned AMPA receptors in Xenopus oocytes has been observed with AS ODNs as short as 8 nt in length. Nevertheless, to be more sure of obtaining sequence specificity, most investigators employ AS ODNs of 15 nt in length or greater. If the AS ODN is made too long, however, partial complementarity may occur with sequences on other RNAs, leading to unintended effects. Indeed, in this regard, shorter oligomers have been found to provide several potential advantages over longer ones, including i) a greater ratio of intended to unintended triggering of RNA degradation compared to longer oligomers, ii) less chance to be prevented from hybridization by secondary structures of the RNA, and iii) faster cellular uptake. The AS ODNs employed typically are between 17 and 26 nt in length. In accordance with the present invention, using an AS ODN targeted to PDE1B1, the preferred PS ODN was of 18 nt in length, which provided the sequence specificity needed for selective inhibition, and still obtain some of the advantages of a somewhat shorter oligomer.

Unfortunately, despite considerable research into this question, the choice of the optimal region of the RNA to be targeted by an AS ODN remains largely empirical. If one has the resources, a way to choose the most effective AS ODN would be to systematically synthesize many AS ODNs targeted to sites along the entire length of the RNA, and test each one out in the system. For those with more limited resources, studies have been done to correlate AS ODN efficacy with regions of secondary structure of the RNA. Initial studies using limited numbers of AS ODNs suggested that three general sites of the RNA might be the most effective to target: i) sequences around initiation codons for translations, II) intron-exon boundaries, and iii) single-stranded loops in hairpin structures. A subsequent study employing 28 different AS ODNs to regions of the procollagen I gene showed that AS ODNs targeted to predicted double-stranded structures of the mRNA were the most effective. This may not always be the case, however, since PS ODNs, depending on their base composition, may have difficulty disrupting double-stranded mRNA secondary structures. When they do disrupt these structures, especially in 3'-untranslated regions, they seem to be very effective, as AS ODNs, perhaps due to destabilizing the mRNA, leading to its more rapid or complete degradation. The greater the GC content of the AS ODN, the greater the chance for it to hybridize and disrupt secondary structures. Therefore, a choice of sites that would result in the production of AS ODNs with >50% GC content would be preferable. Predicted secondary structures for mRNA can be generated by the MFOLD computer program, available through the Genetics Computer Group package distributed by the University of Wisconsin, which predicts optimal and suboptimal secondary structures for RNA molecules using the energy minimization method. An example of a predicted secondary structure of the 5' end of the PDE1B1 mRNA, developed with the MFOLD computer program, is shown in FIG. 1 up to nt 301 in the coding region. The arrow points to the AUG translation initiation start codon, and the draw line indicates the region targeted by the 18 nt PS ODN in accordance with the present invention. This secondary structure map predicts that this AUG start codon of the PDE1B1 mRNA, as well as some flanking bases, do not participate in base pairing to other regions of the RNA, suggesting that AS ODNs might hybridize more easily to the AUG start site than to many of the other regions of the RNA which show appreciable secondary structure as evidenced by the degree of base pairing. For our studies with PDE1B1, we initially targeted this AUG translation initiation region. This decision was based on the thought that i) the AUG site would be accessible for hybridization, ii) we would benefit both from the inhibition of translation as well as the potential for RNase H activation, and iii) because all PDEs share a region of homology of about 270 amino acids toward the 3' end of the coding sequence, an AS ODN targeted to the 5' region would be less likely to have unintended effects on expression of other PDE forms. Since some PDE families, like the PDE4 family, have as many as 15 different splice variants, most of which appear to differ in sequence only at their 5' ends, for PDE forms such as these, one may be restricted to fairly limited regions of unique sequence to target, in order to selectively suppress production of a given isoform. In general, cost permitting, the best approach would be to test at least several AS ODNs targeted to different regions through the RNA, including both the translation initiation region and regions of secondary structure in the 3'-untranslated region.

A recent study of uptake of PS ODNs into human leukemic cells showed that they are taken up both by receptor-mediated and fluid-phase endocytosis, with receptor-mediated endocytosis predominating at lower concentrations. Tracking of labeled PS ODNs by both immunological and ultrastructural means showed the PS ODNs to be present in clathrin coated pits, in endosomal and lysosomal vesicles, and in significant amounts in the nucleus. This, and the many studies showing that PS AS ODNs do have effects when added to cells in culture, indicate that PS ODNs can be taken up by cells and interact with target RNA to suppress expression of a specific gene product. Studies by others, however, failed to detect the presence of PS ODNs in the nuclei of leukemic cells unless cell permeabilization methods were employed, leading to the argument that artificial manipulations to effect intracytoplasmic delivery of ODNs must be undertaken if true antisense effects of ODNs are to be achieved in living cells. Results have clearly shown that enhancing the uptake of ODNs by artificial means can greatly enhance their efficacy. A variety of methods have been successfully employed in order to enhance the uptake of ODNs, including electroporation, membrane permeabilization with streptolysin O, coupling of ODNs to polycations, conjugation of ODNs to fusogenic peptides, targeting of ODNs to specific cell surface receptors, conjugation to cholesterol, and most successfully, complexing ODNs with cationic lipids. Inasmuch as cationic delivery systems are effective, formulated to be optimal for different cell types, and readily available commercially, it is advisable to test one or more of these cationic lipid delivery systems, or cytofectins, as generally termed, with AS ODNs to see if they enhance their efficacy. One of the problems with these cationic lipids, however, is that they are readily broken down in serum, and therefore require an incubation of the cationic lipid-ODN complex with cells in the absence of serum for a period of time, for this delivery to work. This requisite removal of serum from the cells could adversely affect the viability of the cells.

Since PO ODNs are readily and rapidly broken down by nucleases in serum and in cells, with a half-life ≈20 min., it is necessary to take some steps to minimize nuclease action when using unmodified PO ODNs. In particular, cells should be grown in a serum free medium, if possible, or if not, then the serum should be heated at 65° for 1 hr. to heat inactivate the serum nucleases before use. Even so, the nucleases in the cells can cause considerable breakdown of PO ODNs, thus usually requiring much higher levels of these to be added to cells to see effects. Many chemical modifications of PO ODNs, including the PS modification, render them nuclease resistant. The chemistry of these modifications have led to the common use of PS ODNs in place of PO ODNs in many antisense studies. It should be noted, however, that PS ODNs are nuclease resistant, but not nuclease proof. They have been shown to be degraded in tissue culture systems with a half-life of 12–24 hours, although at high concentrations, PS ODNs inhibit nucleases, and the half-life would thus be longer. Hence, for systems involving proteins with very slow turnover rates, that may require a very long incubation of cells with the AS ODN to see an effect, it may be necessary to add the AS ODN on a periodic basis to achieve adequate suppression, even for PS ODNs. One should not make repeated additions of ODNs to cultures indiscriminately, however, since at high concentrations, PS ODNs also inhibit RNase H activity, thereby potentially limiting their effectiveness, and high build up of deoxynucleotides from breakdown of the ODNs could be toxic to cells.

A considerable number of non-sequence-specific effects of ODNs, particularly PS ODNs have been reported, and it is therefore important to do adequate controls to assure that the effects seen are due to sequence-specific antisense mechanisms. While early studies tended to use sense ODN controls, with the sequences complementary to the antisense ODNs, this began to prove inadequate as a proper control, because the sense and antisense ODNs have different base compositions and therefore would generate differing concentrations of deoxynucleotides upon nuclease degradation, and in some systems, the deoxynucleotides generated by breakdown of the ODNs, particularly dGMP and dAMP, were found to have antiproliferative and other biological effects by themselves. Hence, a more preferred control is to use a nonsense ODN (NS ODN), in which the base composition is identical to the AS ODN, but the sequence is rearranged, often in a random manner. This can be accomplished by i) either simply reversing the sequence order of the AS ODN, by making the 3' end of the AS ODN now the 5' end, or ii) by scrambling the bases of the AS ODN, but keeping the base composition the same. Nevertheless, NS ODN controls such as these may still not be sufficient, because certain particular sequence motifs in PS ODNs have been shown to be prone to producing effects by themselves that have nothing to do with the targeted gene sequence. One such motif is a G-quartet, or a string of four contiguous Gs in the PS ODN. Depending on the position of this G quartet in the ODN, and the flanking sequences surrounding it, this G quartet will, to a greater or lesser degree form hyperstructures that result in sequence-independent as well as sequence-specific effects. This is not to say that a PS ODN with such a motif cannot be used. Currently a PS ODN targeted to c-myb, which contains a G quartet, is in clinical trails; however, when such a motif is present in the PS AS ODN to be used, it is necessary to make additional control ODNs that also contain a similar G quartet, albeit with other mismatches in the sequence, in order to be more sure that any effects seen are really due to an antisense effect of the AS ODN. Another sequence motif that can produce biological effects by itself is the presence of a CG in ODNs. Unmethylated CG dinucleotides in DNA, including PS modified ODNs, have been shown to stimulate an immune response in animal models. The cytokines released as a result of this response, particularly IL-12, can result in thrombocytopenia, among other effects. If one is designing an AS ODN for therapeutic application, it might be advisable to be cautious about the presence of a CG motif in the AS ODN to be developed. Certainly, controls employing ODNs with a CG motif surrounded by similar flanking sequences, with other base mismatches present elsewhere in the ODN, should be included especially in in vivo studies that will later be done. In sum, the inclusion of proper and adequate controls is quite important for any antisense study, and the more control ODNs one can include, the more confident one can be that the AS ODN in question is working via a sequence-specific antisense mechanism.

A number of studies had shown that elevated concentrations of cAMP induces apoptosis in lymphoid cells. Since cAMP levels are regulated, in part, by PDEs, inhibition of specific PDE isoforms in lymphoid cells in which they are expressed can induce apoptosis of those cells, without affecting cells which do not express those PDE isoforms. In examining PDEs in lymphoid cells, isolated, quiescent human peripheral blood lymphocytes (HPBL) were devoid of $Ca^{2+}$—calmodulin (CaM)-dependent, PDE1 activity. In contrast, in a B lymphoblastoid cell line derived from a patent with acute lymphocytic leukemia, PDE1 constituted the majority of the PDE activity. The PDE1 isoform(s) expressed in RPMI 8392 cells, as well as other lymphoid cells expressing PDE1 activity were selectively inhibited to induce apoptosis in these cells without affecting isolated, quiescent HPBL. The PDE1 gene family consists of at least three different genes, with multiple splice variants, and hence, to selectively inhibit the PDE form(s) expressed in the RPMI 8392 cells, we employed an antisense approach. By reverse transcription-polymerase chain reaction (RT-PCR), the RPMI 8392 cells were shown to express the mRNA for PDE1B1. HPBL in the quiescent state does not express this mRNA, although they do so following mitogen stimulation. Also using RT-PCR, one can clone and sequence the cDNA for PDE1B1 from RPMI 8392 cells, which then enables one to prepare and test AS ODNs targeted to this gene.

Figure 2A:
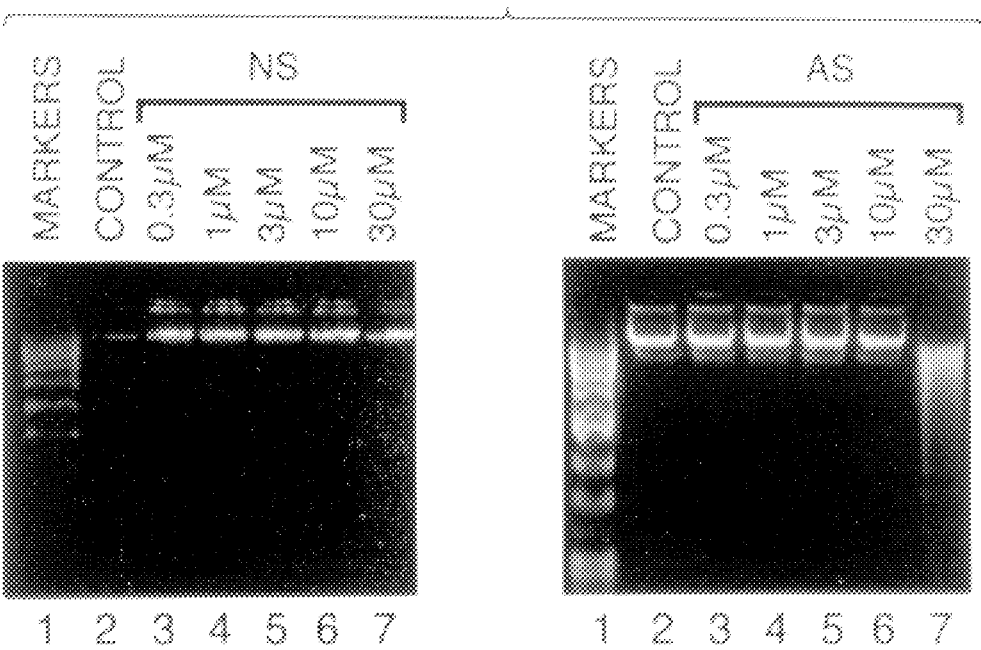
FIGS. 2A and 2B are a series of photographs showing the induction of apoptosis with different concentrations of AS ODN and NS ODN.
Figure 2B:
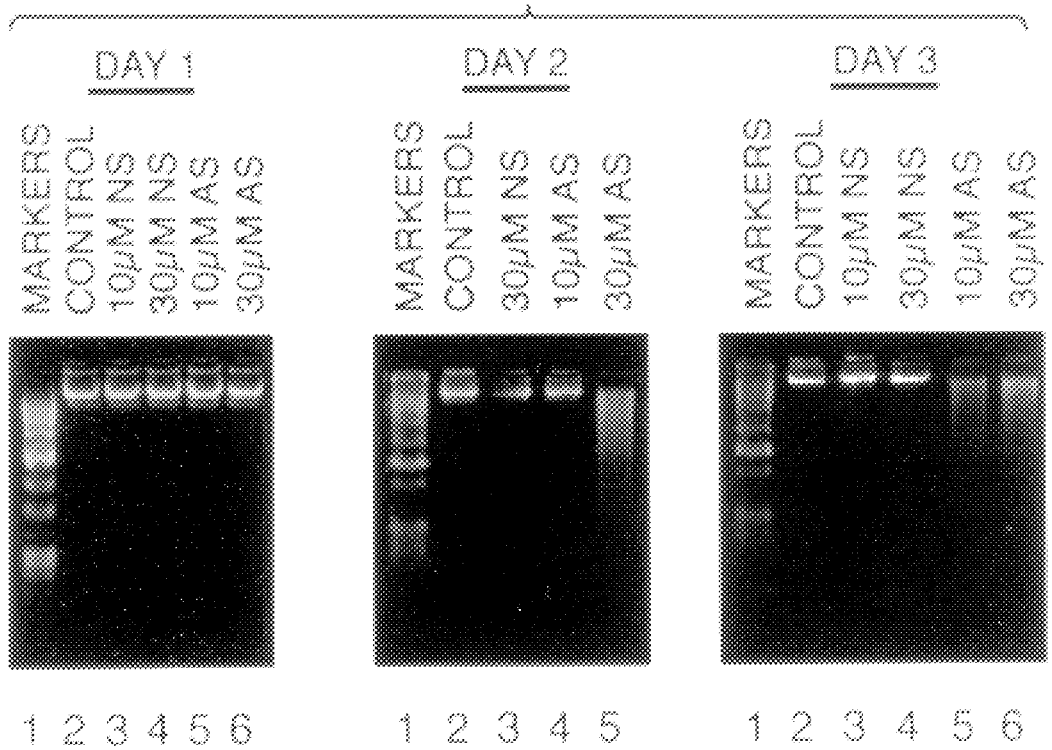

The targeted site of the PDE1B1 mRNA was the translation initiation region. We made a PS ODN 18 nt in length, beginning in the 5'-untranslated region, six bases upstream of the AUG start codon, and extending 12 bases, or 4 codons, into the coding region. The sequence of this portion of the target PDE1B1 cDNA was 5'-CTGAGCATGGAGCTGTCC-3' (SEQ. ID NO:4), and the sequence of the PS ODN prepared was the exact reverse complement of this, or 5'-GGACAGCTCCATGCTCAG-3' (SEQ. ID NO:5). This AS ODN contains no G quartet, no CG motif, and 11 of the 18 bases are G or C, giving it a GC content≈61%. A control NS ODN was also prepared, by randomly scrambling the sequence of the AS ODN, and the sequence of the NS ODN thus prepared was 5'-TACGTGAGGCACCTACGC-3' (SEQ. ID NO:6). Both the AS ODN and the NS ODN were tested in concentrations from 0.3–30 µM for their ability to induce apoptosis of RPMI 8392 cells, as assessed by the appearance of oligonucleosome length fragments of endonuclease-digested DNA on agarose gels, following incubation with the cells, by procedures described in detail hereinafter. As shown in FIG. 2, the AS ODN induced apoptosis at 30 µM after 2 days and at 10 and 30 µM after 3 days, whereas the NS ODN had no effect at any of the concentrations tested.

Figure 4:
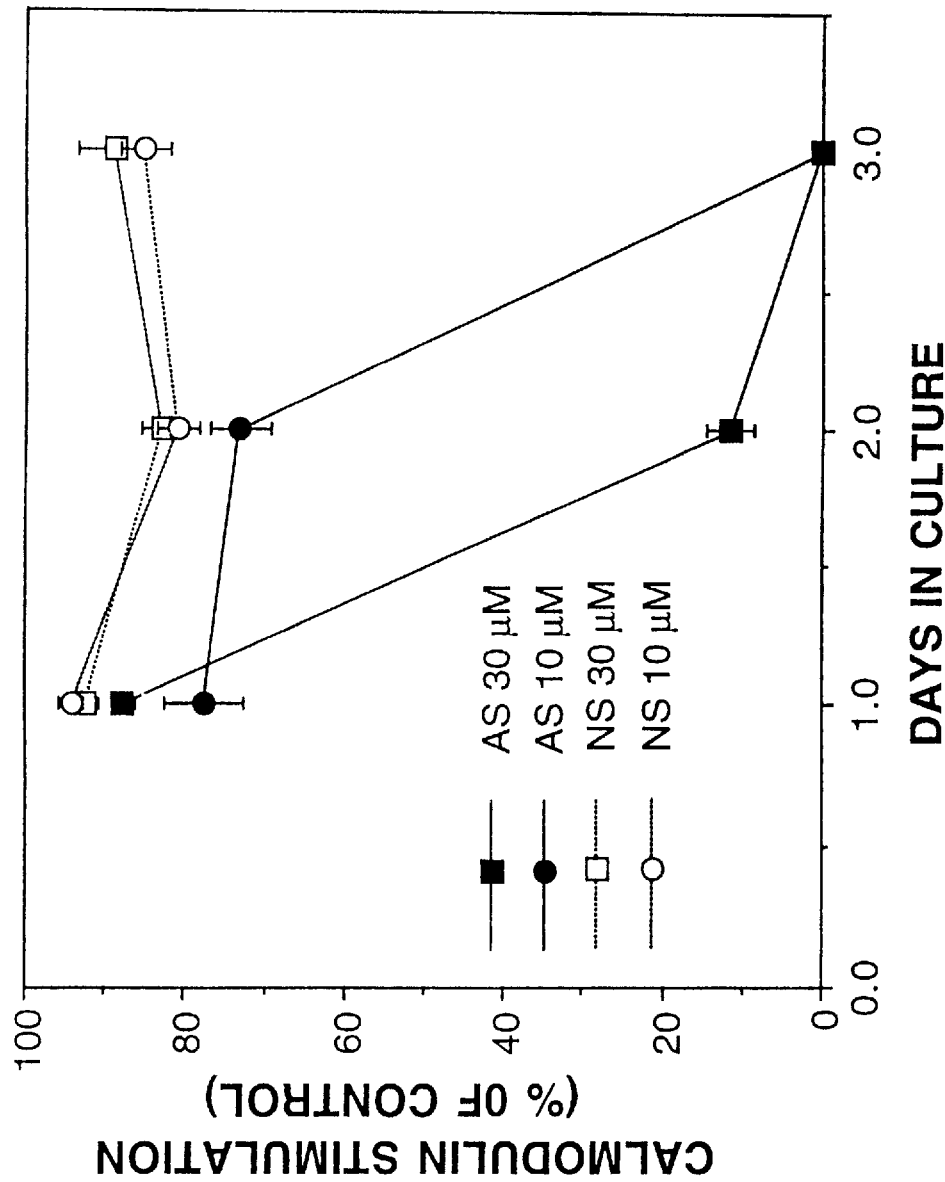
FIG. 4 is a graph showing the disappearance of PDE1B1 activity following AS ODN treatment.

To be certain that the antisense is working as intended, it is necessary to demonstrate that the expression of the gene targeted is indeed suppressed. This is usually determined by looking at the reduction or disappearance of the protein product, either by selective measurement of an enzymatic activity of the protein, where applicable, or by immunoquantitation with specific antibodies by Western blot or ELISA techniques. Also, when PO or PS ODNs are used, which are capable of activating RNase H activity, it is expected that the mRNA of the targeted gene would be down regulated, most of the time, along with the protein product, and this can be readily tested by Northern blot analysis or PCR techniques. Using quantitative RT-PCR with primers specific for PDE1B1, we examined the RPMI 8392 cells for the presence of PDE1B1 mRNA. As shown in FIG. 3, the level of PDE1B1 mRNA expression was diminished after 1 day in cells treated with 10 or 30 µM AS ODN, and was almost undetectable after 2 days. NS ODN, at these concentrations, had no effect on the expression of PDE1B1 mRNA. An additional control employed in ODN antisense studies is to show that expression of a gene other than the one targeted by the AS ODN is unaffected by treatment of the cells with the ODNs. In this connection, the expression of β-actin is unaffected by cAMP and, therefore, β-actin mRNA levels were used as a control. Another gene that is often also used for control measurements for this purpose is that of glyceraldehyde-3-phosphate dehydrogenase (G3PDH). FIG. 3 shows that the levels of β-actin mRNA were unchanged by AS ODN or NS ODN treatment. Enzymatic analysis of PDE1 activity, graphically illustrated in FIG. 4, showed it to be noticeably diminished after 2 days treatment with 30 µM AS ODN and to disappear completely after 3 days treatment with either 10 or 30 µM AS ODN. NS ODN had little or no effect on PDE1 activity at these concentrations.

Another control to ensure that the effects seen are due to antisense mechanism is to show that the AS ODN produces no effect in cells that do not express the gene to which it is targeted. Since isolated, quiescent HPBL does not express PDE1B1, HPBL can be used as control cells in which to test for an absence of an AS ODN effect. One problem with use of HPBL, however, is that quiescent B lymphocytes were reported to undergo spontaneous apoptosis as soon as they were isolated and placed in culture, without any stimulus, as is commonly seen with many types of cells that are removed from growth or viability factors, and this has been observed to be true for HPBL as well. Nevertheless, the effects of AS ODNs on HPBL can still be tested by quantifying and comparing the percentage of cells undergoing apoptosis in the presence and absence of the AS ODN. Apoptosis detected by examining endonuclease-digested DNA, commonly referred to as the DNA laddering technique, has been employed and the results therefrom are set forth in FIG. 5. However, we prefer to use a TUNEL assay, an acronym for terminal deoxynucleotidyl transferase (TdT)-mediated d UTP nick end labeling, which more readily allows quantitation of the percentage of cells undergoing apoptosis. The principle of the TUNEL assay is that endonuclease digestion during apoptosis results in the formation of 3'-OH ends in the digested DNA. The digested DNA in the apoptotic cells can then be labeled with fluorescein by catalytically incorporating fluorescein-12-dUTP at the 3'-OH ends using the TdT enzyme. Fluorescence can then be quantitated by flow cytometry, using a fluorescence activated cell sorter (FACS), which would give a measure of the number of cells undergoing apoptosis. An example of the appearance of a population of fluorescein labeled apoptotic cells, as evidenced by flow cytometry, following TUNEL assay labeling of the cells, is shown in FIGS. 6A–C. Cells were then cultured for 3 days with 10 µg/ml PHA-P (Sigma), in the absence of any ODN (FIG. 6A), in the presence of 30 µM NS ODN (FIG. 6B), or in the presence of 30 µM AS ODN (FIG. 6C). Cells were then collected by centrifugation and fluorescein labeled by the TUNEL assay using the Promega Apoptosis Detection System. Flow cytometry was performed on a Beckton Dickinson FACScan by the FACS facility. The arrow in FIG. 6C shows an example of the region of cell population that is more highly labeled with fluorescein, indicative of apoptotic cells. The area under this region was calculated, for each different condition, to derive the % apoptotic cell data displayed in FIG. 7. Thus, this figure shows that after 3 days treatment with AS ODN, phytohemagglutinin (PHA)-stimulated HPBL show the appearance of a population of highly fluorescein labeled cells, indicative of apoptosis, whereas PHA-stimulated HPBL treated with NS ODN or no ODN, do not show the appearance of this population of more highly labeled cells.

Figure 6A:
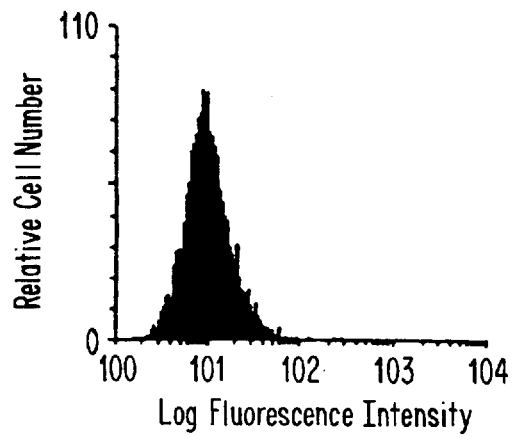
FIGS. 6A–6C are graphs showing a flow cytometry analysis of HPBL cells labeled with fluorescein by the TUNEL assay.
Figure 6B:
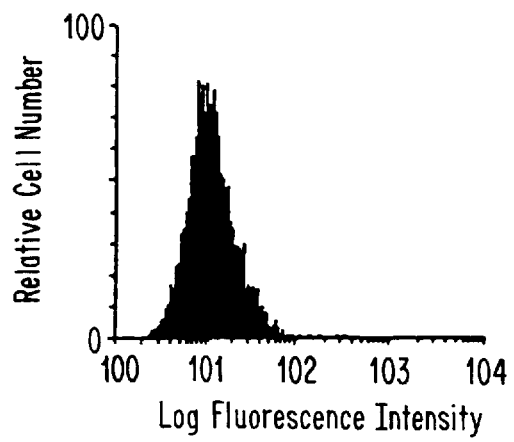
Figure 6C:
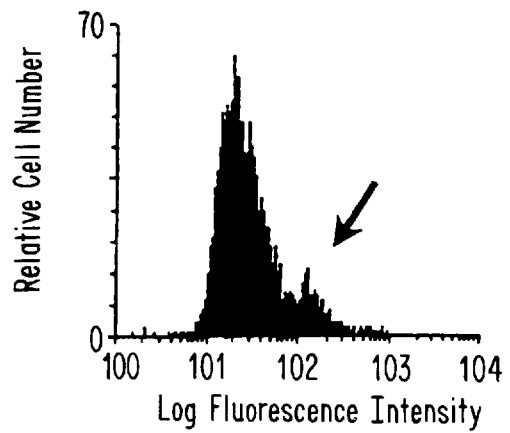
Figure 7:
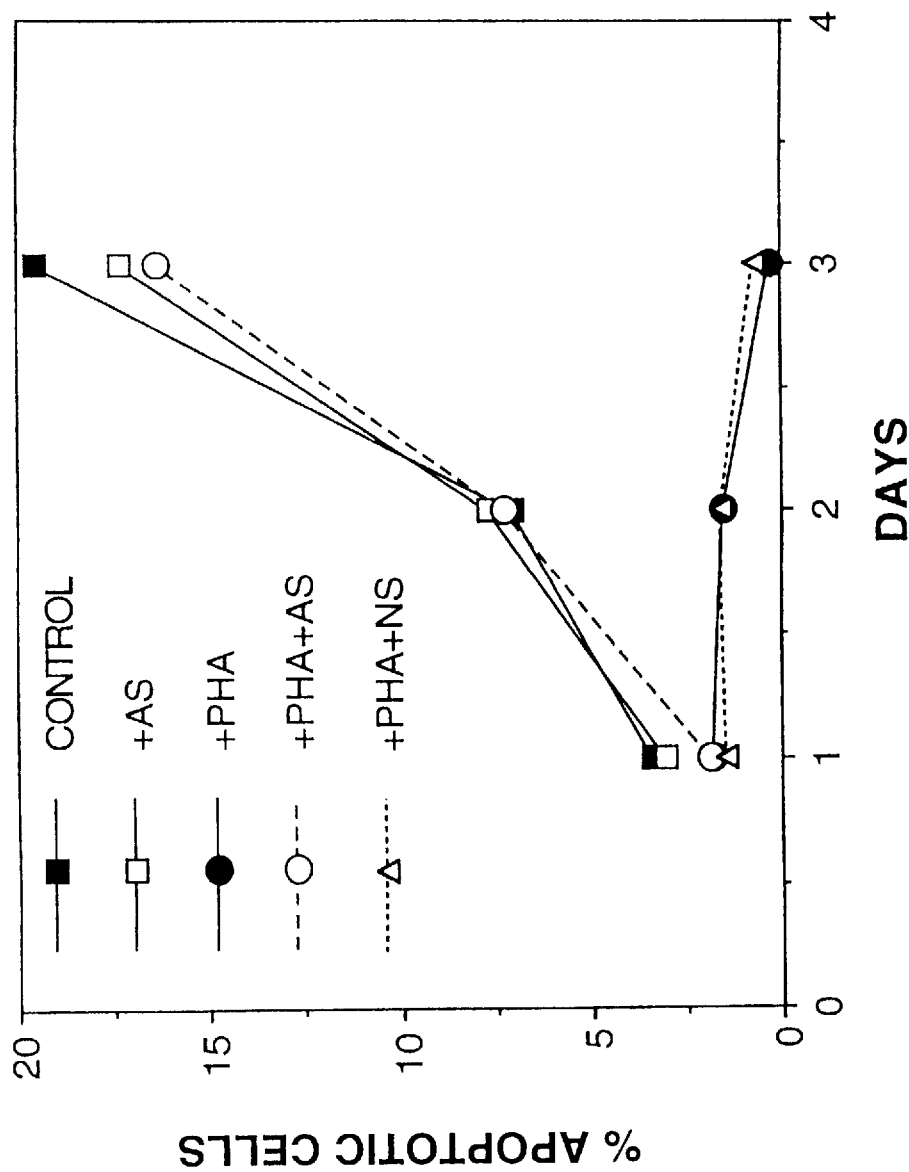
FIG. 7 is a graph showing the results of the TUNEL assay of apoptosis in HPBL.

Using the TUNEL assay, we found that isolated, quiescent HPBL placed into culture begin to undergo apoptosis spontaneously, without any added stimulus, at a rate somewhat similar to that reported for peripheral blood B cells. The rate of formation of apoptotic HPBL cells was unchanged by addition of AS ODN, indicating that the AS ODN produced no noticeable effect on quiescent HPBL, as expected, since these cells do not express PDE1B1. Results with addition of NS ODN alone (not shown) were also no different from control. We found, however, that when the mitogen, PHA was added to the HPBL in culture, it prevented the HPBL from undergoing spontaneous apoptosis (FIGS. 6 and 7). Since PHA induces the expression of PDE1B1 in HPBL, addition of AS ODN to PHA-stimulated HPBL would be expected to have an effect on these cells. Indeed, AS ODN induced apoptosis in the PHA-treated HPBL, at a rate now similar to that of resting HPBL undergoing spontaneous apoptosis, whereas NS ODN had no effect as shown in FIGS. 6 and 7).

The preferred method for testing the ability of AS ODN to induce apoptosis as determined by detection of endonuclease digested DNA on agarose gels employs the following sequence:

(1) RPMI 8392 or other lymphoblastoid cells are maintained in culture in humidified air/5% $CO_2$ at 37° C. in a growth medium consisting of RPMI 1640 medium supplemented with 10% fetal bovine serum, 100 units/ml penicillin, 100 μg/ml streptomycin and 2 mM L-glutamine.

(2) Cells are grown to ≈$10^6$/ml, collected by centrifugation for 5 min. at 300×g (1000 rpm in an IEC Model K centrifuge), resuspended in growth medium to $10^6$ cells/ml, and placed in a 24 well tissue culture plate at 1 ml/well. The cell volumes are kept to a minimum (i.e., ~1 ml), in order to reduce the amount of ODN needed. The fetal bovine serum used in the growth medium for this step is heat-inactivated at 65° C. for 1 hr. to minimize serum nuclease activity.

(3) ODNs are dissolved in RPMI 1640 medium to a concentration of 1 mM. Serial dilutions of this stock are made at half-log units and 30 μl are added to the 1 ml cell suspensions in the wells (1:33.3 dilution) to give the desired final concentrations.

(4) Cells are then incubated for varying times, usually 1–3 days, following which the DNA is isolated.

(5) For isolation of the DNA, cells are collected by centrifugation at 300×g for 5 min., rinsed in phosphate buffered saline (137 mM NaCl, 2.68 mM KCl, 10 mM $Na_2HPO_4$, 1.76 mM $KH_2PO_4$, pH 7.4) by centrifugation at 300×g for 5 min. The supernatant is aspirated down to ≈50 μl of volume and the cell pellet is resuspended in this remaining small volume.

(6) About 400 μl of cold cell lysis buffer (50 mM Tris-HCl, pH 7.5, 10 mM EDTA, 1% Triton X-100) is then added. The cells are pipeted up and down several times in the buffer and incubated on ice for 20 min.

(7) Proteinase K is then added to a concentration of 0.5 mg/ml from a stock concentration of 15 mg/ml in pH 8.0 TE buffer (10 mM Tris-HCl, pH 8.0, 1 mM EDTA, pH 8.0), and incubation is carried out at 37° C. for 30 min.

(8) An equal volume (≈0.5 ml) of phenol is then added, the mixture gently vortexed for 5 sec., and centrifuged at 16,650×g (14,000 rpm in an Eppendorf Model 5415 microcentrifuge) for 10 min. at 4° C.

(9) The upper, aqueous phase is transferred to a fresh microfuge tube and 250 μl of phenol and 250 μl of chloroform are added, the mixture gently vortexed for 5 sec., and centrifuged at 16,650×g for 5 min.

(10) The upper, aqueous phase is again transferred to a fresh microfuge tube and 500 μl of chloroform is added, followed by gentle vortexing and centrifugation at 16,650×g for 3 min.

(11) The upper, aqueous phase is again transferred to a fresh microfuge tube, 3M sodium acetate (pH 5.2) is added to a final concentration of 0.3M, and 2.5 volumes of ice cold 100% ethanol is added. The solution is left overnight at −20° C. to precipitate the DNA.

(12) The DNA is collected by centrifugation at 16,650×g for 15 min., the supernatant decanted, and the pellet air dried for ≈30–60 min. at room temperature. The DNA pellet is then dissolved in 50 μl of pH 8.0 TE buffer at room temperature overnight.

(13) One μl of a 4 mg/ml solution of DNase-free RNase A is then added to the DNA and incubation is carried out at 37° C. for 30 min. This step is necessary to prevent contaminating RNA from obscuring the gel.

(14) Thirty μl of DNA solution is then mixed with 6 μl of 6× loading buffer and run on a 2% agarose gel, containing 0.5 μg/ml ethidium bromide, in 0.5× TBE buffer (45 mM Tris-borate, 1 mM EDTA, pH 8.0) at ≈50 V for ≈1.5 hr. The 6× loading buffer used is 0.25% xylene cyanol and 30% glycerol. The use of bromophenol blue is omitted for this analysis because it tends to obscure the visualization of the DNA ladder pattern.

(15) The gel is then visualized and photographed under UV light.

The procedure for analyzing apoptosis by the TUNEL method uses either an In Situ Cell Death Kit, Fluorescein from Boehringer Mannheim or an Apoptosis Detection System, Fluorescein from Promega and follows the protocols of the manufacturers. The data in FIGS. 6 and 7 was obtained using the manufacturer's protocol for the Apoptosis Detection System, Fluorescein from Promega.

Isolation and Purification of HPBL

HPBL were purified from 30–60 ml of blood obtained from normal donors by defibrination with glass beads to remove platelets, incubated with tetracarbonyl iron to minimize monocyte contamination and centrifuged on Ficoll-Hypaque density gradients to achieve cell separation. Purity of the lymphocytes achieved by this procedure was >98% by light microscopic analysis. For mitogenic stimulation, HPBL were suspended in RPMI 1640 medium supplemented with 10% autogolous serum, 100 U/ml penicillin, 100 μg/ml streptomycin, 2 mM L-glutamine, at $10^6$ cells/ml and stimulated either with 10 μg/ml phytohemagglutin-P (Sigma), 1 mM dbcAMP (Sigma), 0.1 mM IBMX (Aldrich), or a combination of 1 mM dbcAMP and 0.1 mM IBMX as indicated, at 37° C. in a humidified atmosphere of 5% $CO_2$ in air for the times indicated. For this stimulation, cells were placed in 25 $cm^2$ flasks in a total volume of 10 ml/flask.

Source and Maintenance of Lymphoid Cell Lines

The B lymphoblastoid cell line, RPMI 8392, was established from a patient with acute lymphocytic leukemia. The T leukemic cell line, Molt 4, was obtained from the American Type Culture Collection, Rockville, Md. Both cell lines were maintained and grown in suspension at 37° C. in a humidified atmosphere of 5% $CO_2$ in air in RPMI 1640 medium supplemented with 10% heat-inactivated (56° C., 30 min.) fetal calf serum, 100 U/ml penicillin, 100 μg/ml streptomycin, 2 mM L-glutamine, as described previously.

RT-PCR Protocol

Total RNA was isolated from ≈$2-5\times10^6$ HPBL, RPMI 8392 and Molt 4 cells using TRIzol Reagent (GIBCO/BRL) according to the manufacturer's instructions. First strand cDNA was synthesized from the RNA using a Superscript Preamplification System from GIBCO/BRL. Total RNA (5 μg) isolated from HPBL, RPMI 8392, and Molt 4, respectively, was reverse transcribed by mixing with 10 pmoles random primer followed by heating to 70° C. and subsequent cooling. To this was added 10 mM Tris/HCl pH 8.4, 50 mM KCl, 2.5 mM $MgCl_2$, 10 mM DTT, 500 μM each of dGTP, dATP, dCTP and dTTP in a total volume of 20 μl, and the resultant mix was incubated at room temperature for 5 min. Superscript II reverse transcriptase (2 U) was then added and incubation continued at 42° C. for 50 min. at 70° C. for 15 min. RNase H (2 U) was then added and incubation carried out for 20 min. at 37° C. PCR amplification was carried out in a total volume of 50 μl using 2 μl of cDNA, 20 mM Tris/HCl pH 8.4, 50 mM KCl, 1.5 mM MgCl$_2$, 200 μM each of dGTP, dATP, dCTP and dTTP and 0.4 μM of sense and antisense primers specific for different isogenes of human PDE4, human β-actin and human PDE1B1, as described hereinafter. The PCR reaction mixture was incubated at 94° C. for 5 min. followed by the addition of 0.5 μl Taq DNA polymerase (5 U/μl, GIBCO/BRL). PCR amplification was then carried out for 35 cycles at 94° C. for 1 min., 58° C. for 1 min., 72° C. for 1 min., followed by a final extension at 72° C. for 10 min., except where indicated otherwise. A sample of amplified DNA (10 μl) was resolved on a 1.5% agarose gel containing 0.5 μg/ml ethidium bromide and visualized and photographed under UV light. Controls in which reverse transcriptase was omitted from the first strand cDNA synthesis and cDNA was omitted from the PCR amplification reaction showed no discernable product. PCR amplification with primers specific for human β-actin were run for every cell sample, as positive controls to ensure that the isolated RNA was not degraded, and for normalization to verify that relatively equal amounts of RNA were used for the first strand cDNA synthesis reactions. It has been shown previously that cAMP does not affect the expression of the mRNA for β-actin.

PCR Primers

Primers specific for PDE4A, PDE4B, PDE4C, and PDE4D3 were synthesized. The primers specific for PDE4A would amplify a 907 nt fragment common to all cloned forms of human PDE4A that encode an enzymatically active protein: HSPDE4A4A (h-PDE1), GenBank accession no. M37744; HSPDE4A4B (PDE-46), GenBank no. L20965; HSPDE4A4C (h6.1), GenBank no. U18087. The fragment amplified corresponds to nt 701–1607 in M37744, nt 1148–2054 in L20965 and nt 442–1348 in U18087. These primers would also amplify nt 1034–1939 in the inactive variant, TM3 (GenBank no. L20967), but would not recognize the inactive variant hPDEIVA-2el (HSPDE4A8, GenBank no. U18088). Primers specific for PDE4B would amplify a 625 nt fragment found in all cloned forms of human PDE4B. The fragment thus amplified would correspond to nt 1046–1670 in GenBank no. L20966, nt 673–1297 in M97515, nt 1157–1781 in L20971, and nt 586–1210 in L12686. Primers specific for PDE4C would amplify a 289 nt fragment in one of the cloned forms of human PDE4C, corresponding to nt 2231–2519 in GenBank no. Z46632 or nt 744–1032 in L20968, but would not recognize the two forms of PDE4C that were just cloned, GenBank nos. U88712 and U88713. The primers specific for PDE4D3 would amplify a 642 nt fragment in the cloned forms of human PDE4D3, corresponding to nt 374–1015 in GenBank no. L20970 (PDE43), nt 144–785 in U02882 (hPDEIVD), and nt 317–958 in U50159, and the cloned form of PDE4D4, corresponding to nt 1052–1693 in L20969 (PDE39). The sense primer of this PDE4D3 specific pair would not, however, recognize the cloned forms of PDE4D1 and PDE4D2, as described by Nemoz et al. Therefore, in order to amplify fragments of PDE4D1 and PDED2, a sense primer corresponding to the first 18 nt of both of these clones was prepared, with the sequence 5'-GTATGGCAGGATGGCCCC-3' (SEQ. ID NO:7). This sense primer, when used with the antisense primer originally designed for PDE4D3 would amplify a 623 nt fragment for PDE4D1, corresponding to nt 1–623 in GenBank no. U50157 and a 537 nt fragment for PDE4D2, corresponding to nt 1–537 in U50158. Gel analysis resolves two fragments using these primers, one for PDE4D1 and one for PDE4D2, 86 nt different in size, since the sequences of these two variants are the same except for an 86 nt insert in PDE4D1, within the region encompassed by these primers. Most of the time, with these primers, two bands of the predicted fragment sizes are seen upon gel resolution; however in some cases three rather than two bands represented the correct products and all three bands are isolated from the gel and sequenced. The uppermost band was a non-specific product, since its sequence did not match any known form of PDE, whereas the sequence of the middle band clearly matched that of PDE4D1 and the lower band clearly that of PDE4D2. Primers specific for human β-actin were synthesized and amplify a 396 nt fragment corresponding to nt 42–437 in human β-actin, GenBank no. X00351. Primers specific for PDE1B1 were primers 3 and 4, as described herein in connection with FIG. 8. These primers amplify an 854 nt fragment corresponding to nt 14–867 in GenBank no. U56976.

Expression of PDE1B1 in Mitogen-Activated and Cultured Lymphoblastoid Cells

Calmodulin-dependent PDE activity (PDE1) has been shown to be present in a human B lymphoblastoid cell line, RPMI 8392, isolated from a patient with acute lymphocytic leukemia, but absent from normal, resting HPBL. The PDE1 gene family is comprised of at least 3 different genes, some producing alternate spliced forms as well. Using quantitative RT-PCR, resting and mitogen stimulated HPBL and RPMI 8392 cells for the presence or absence of mRNA for the 63 kDa form of PDE1 (PDE1B1), using degenerate primers specific for this form of PDE.

HPBL were isolated from a normal human donor and placed in culture with (+PHA) or without (−PHA) phytohemagglutinin for 3 days. Quantitative RT-PCR was performed with 2 μg of HPBL RNA, using reagents and protocol from GIBCO/BRL. Degenerate 23 nt primers were synthesized based on reported sequences for PDE1B1. The sequence of the forward primer (Primer 1) corresponds to nt −34 to −12 and the sequence of the reverse primer (Primer 2) is complementary to nt 277 to 299 of the PDE1B1 cDNA. PCR amplification was carried out for 5 cycles at 94° C. for 1 min, 60° C. for 1 min, and 72° C. for 1 min, after which forward and reverse primers specific for a 250 nt fragment of β-actin were added to the reactions, and PCR amplification continued for another 20 cycles, followed by a final extension at 72° C. for 10 min. Amplified DNA was resolved on a 1.5% agarose gel containing 0.5 μg/ml ethidium bromide and visualized and photographed under UV light. Samples applied to the agarose gel were as follows, lane 1: 1 kb DNA ladder size markers (GIBCO/BRL); lane 2: unstimulated HPBL (−PHA) RT-PCR product; lane 3: phytohemagglutinin-stimulated HPBL (+PHA) RT-PCR product.

Figure 9:
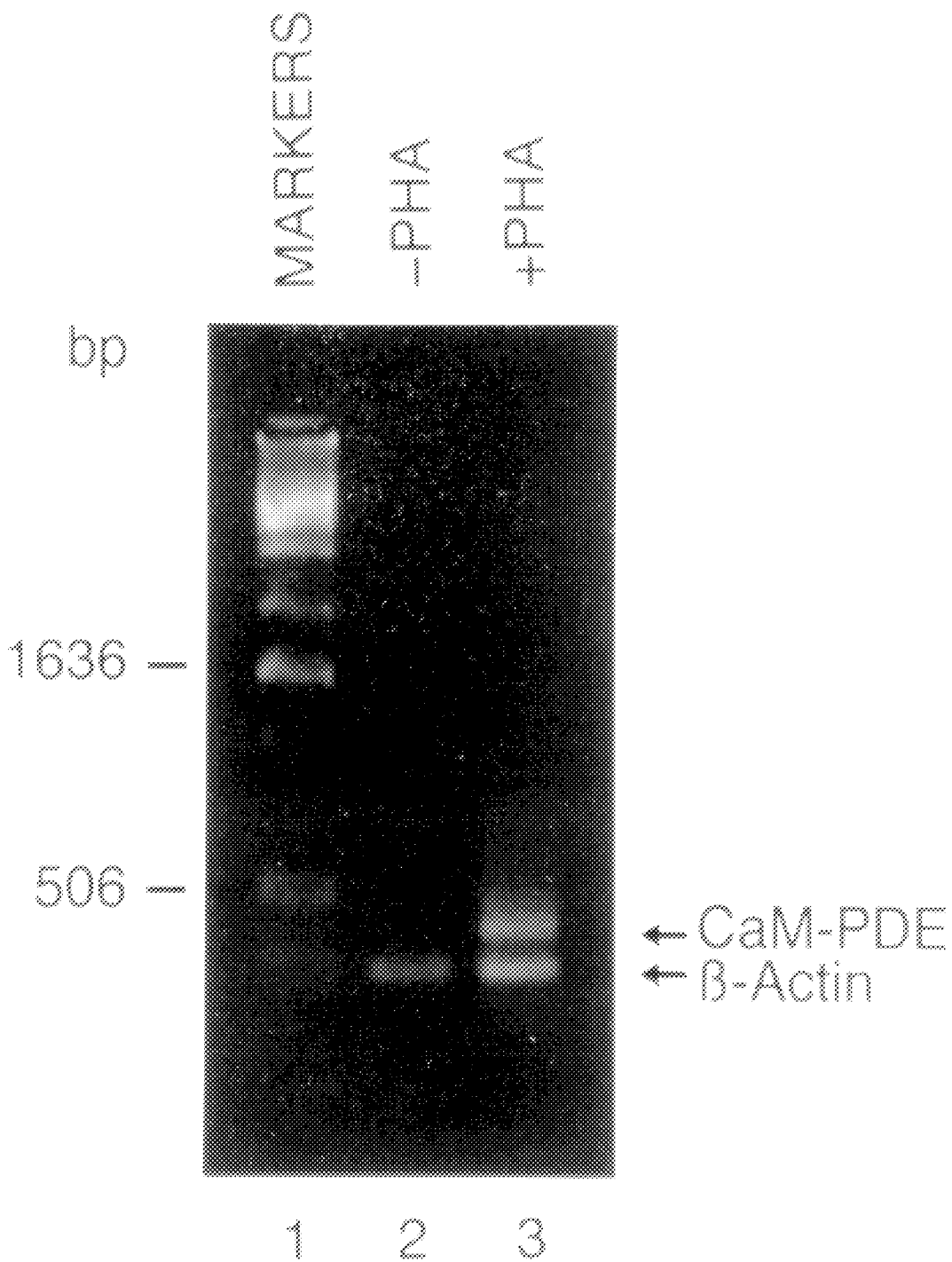
FIG. 9 is a photograph of a DNA gel separation showing the expression of PDE1B1.

As shown in FIG. 9, HPBL stimulated by the mitogen, PHA, for 3 days, show a cDNA fragment of the predicted size of ≈333 nt, whereas unstimulated HPBL do not. Primers specific for human β-actin, included as a control in the same reactions, show similar amounts of β-actin present in both resting and PHA stimulated HPBL, indicating that the absence of a fragment corresponding to PDE1B1 in resting HPBL is not due to nonspecific breakdown of the mRNA, and that equal amounts of template mRNA were added to each of the RT-PCR reactions. mRNA isolated from RPMI 8392 cells and similarly subjected to RT-PCR also produced the 333 nt DNA fragment expected for PDE1B1 (not shown). Sequence analysis of the 333 nt fragments from PHA-treated HPBL and RPMI 8392 cells show the two to be 100% identical to one another and to share 95% nt identity to bovine PDE1B1. Hence, the cDNA fragments produced by RT-PCR clearly belong to the PDE1B1 gene family.

Growth and Maintenance of Cells

The B cell lines RPMI 8392 and RPMI 1788, and the T cell lines NA, JB and Daudi were established from patients and provided by other investigators. The T cell lines Jurkat and Molt 4 were obtained from the American Type Culture Collection. HPBL were isolated from 60 ml of freshly drawn blood from normal donors by defibrination with glass beads and separation of the lymphocytes by Ficoll-Hypaque density gadient centrifugation. When stimulated by mitogen, HPBL were suspended in RPMI 1640 medium supplemented with 10% autologous serum, 100 units/ml penicillin, 100 μg/ml streptomycin, 2 mM L-glutamine, and stimulated with 10 μg/ml phytohemagglutinin-P (Sigma) for 3 days.

Cloning of the Full cDNA ORF for Human PDE1B1

Since the full sequence for the human form of PDE1B1 has not been reported, in order to obtain this sequence, we cloned the cDNA for PDE1B1 from RPMI 8392 cells by RT-PCR.

Production and Sequence of Human 63 kDa CaM-PDE cDNA

The cDNA for the human 63 kDa CaM-PDE was produced and amplified from RPMI 8392 cells by RT-PCR. Total RNA (5 μg) isolated from RPMI 8392 cells was reverse transcribed with random primers and the DNA amplified by PCR with reagents and protocol from GIBCO/BRL using forward and reverse primers specific for different regions of PDE1B1 containing Not I restriction sites and 10 random nt on their 5'-ends, for subsequent subcloning. Amplification was for 35 cycles at 94° C. for 1 min, 5° C. for 1 min, and 72° C. for 1.5 min. The PCR products were separated on 1.5% agarose gels, purified, and sequenced directly, and then subcloned into p-Bluescript and sequenced again. Sequencing was performed using the same primers as for PCR, as well as other oligodeoxynucleotide primers derived from the sequences obtained, and T3 and T7 primers for sequencing of the subcloned inserts.

cDNAs corresponding to regions spanning from nt −23 to 834 and nt 729 to 1611 of PDE1B1 were generated and sequenced, and together they encompass the full ORF of the human form of PDE1B1. Attempts to do RT-PCR using degenerate primers corresponding to regions of the 3'-untranslated sequence did not produce a product, and thus a degenerate primer corresponding to the last 25 nt of the 3'-end of the ORF was used instead. The sequence of this 3'-end of the ORF and the 3'-untranslated sequence were obtained by PCR of a human brain cDNA library.

Overlapping RT-PCR products were made from RPMI 8392 cell RNA and sequenced, as reported in FIG. 8. Nucleotide and amino acid numbering are indicated at the left, with positions in the 5'-untranslated region indicated as negative numbers. 5'-untranslated sequence is presented in lower case, and ORF sequence in capitals. Primer sequences were based on reported sequences for PDE1B1 from other species. The forward primers were Primer 3, nt −23 to 3 and Primer 5, nt 729 to 752. The reverse primers were Primer 4, complementary to nt 810 to 834 and Primer 6, complementary to nt 1587 to 1611. PCR of a human temporal cortex cDNA library (Stratagene) was accomplished with a primer from nt 1509–1532 (Primer 7), and T7 primer. Primers 2–7 are underlined and Primer 1 is overlined. The TAG termination codon is marked by an asterisk. The 3'-untranslated sequence is given up to the Eco RI cloning site in the vector. The nucleotide degeneracy is as follows: R=A or G, M=A or C, Y=C or T.

As shown in FIG. 8, PDE1B1 in RPMI 8392 cells has an ORF of 1611 nt, encoding a predicted protein of 536 aa. The predicted protein shares 96% aa identity with PDE1B1 from bovine, rat, and mouse, indicating a very high degree of sequence homology for this protein across species.

Induction of Apoptosis in RPMI 8392 Cells by Pharmacological Inhibitors of PDE1 and PDE4

Analysis of cytosolic extracts of RPMI 8392 cells by DEAE anion exchange chromatography yielded two peaks of activity with properties representative of PDE1 and PDE4. The effect of pharmacological inhibition of each of these PDE activities on induction of apoptosis in RPMI 8392 cells was tested, using the appearance of oligonucleosome length fragments of endonuclease digested DNA as a measure of apoptosis.

DNA from RPMI 8392 cells was isolated and analyzed for fragmentation on 2% agarose gels, after culture for 24 hr without (Control) or with different concentrations of the PDE inhibitors vinpocetine (lanes 3–6, left gel), RO 20–1724 (lanes 3–6, right gel), and rolipram (lanes 7–10, right gel), as indicated. Markers (lane 1 in both gels) are 1 kb DNA ladder size markers from GIBCO/BRL.

Figure 5:
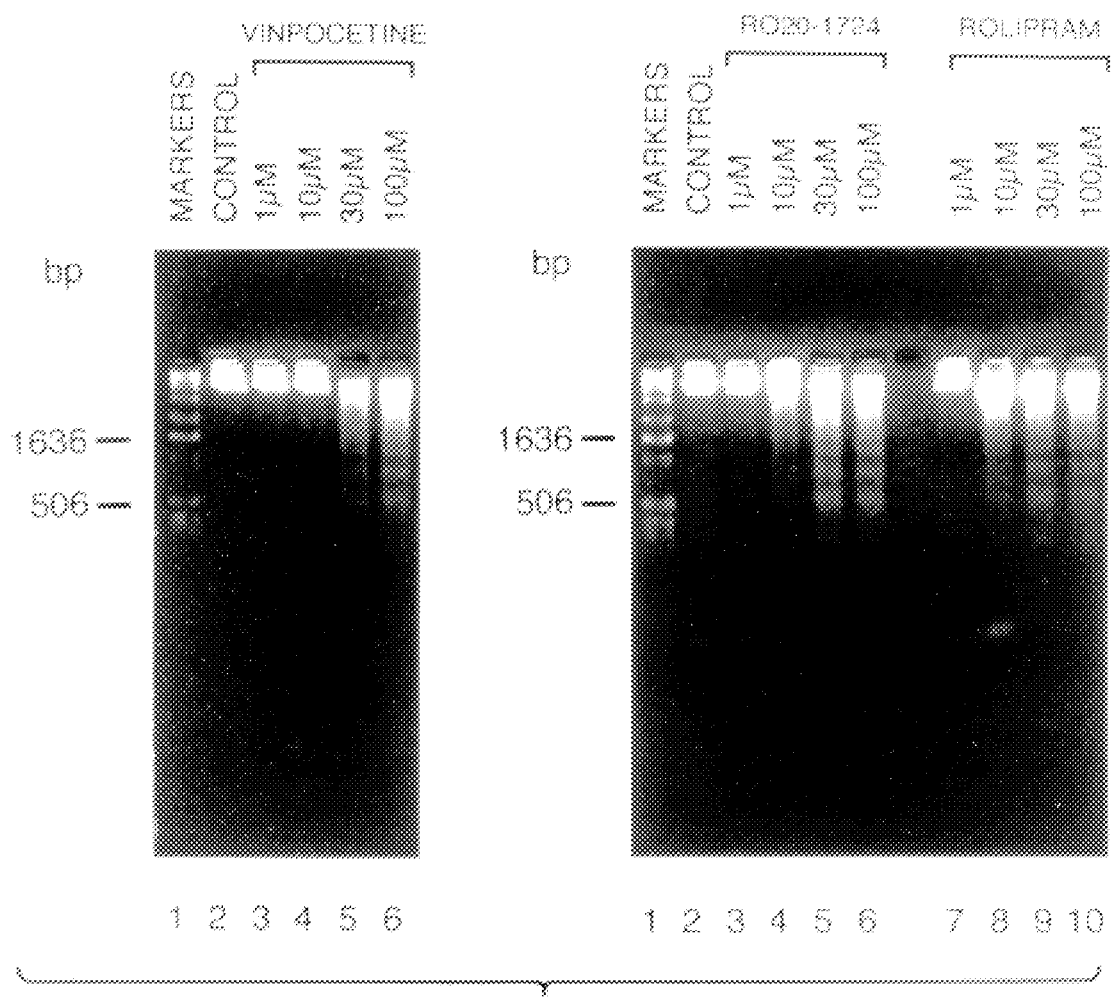
FIG. 5 is a photograph of a gel showing the laddering pattern indicative of apoptosis with different concentrations of different PDE1 and PDE4 inhibitors.

As shown in FIG. 5, vinpocetine, a selective inhibitor of PDE1, induced apoptosis in these cells at concentrations $\geq$30 μM; rolipram and RO 20–1724, selective inhibitors of PDE4, each induced apoptosis at concentrations $\geq$10 μM. The effects of these inhibitors on PDE activity was examined in whole cell homogenates of RPMI 8392 cells.

PDE activity in whole cell homogenates of RPMI 8392 cells was tested for sensitivity to inhibition by vinpocetine, RO 20–1724, and rolipram, as indicated. Cells were grown to a density of about $10^6$/ml, collected by centrifugation (1200×g, 10 min), resuspended in I ml of homogenization buffer containing 40 mM Tris/HCl (pH 7.5), 1 mM EDTA, 1 mM DTT, 35 μg/ml phenylmethylsulfonyl fluoride, 15 mM benzamidine, 1 μg/ml leupeptin, 1 μg/ml antipain, 1 μg/ml pepstatin, and 1 μg/ml aprotinin, homogenized with 20 strokes of a Dounce glass-on-glass homogenizer and assayed for PDE activity, using 1 μM cAMP as substrate, as described previously. Data points represent the means of 2 to 10 separate determinations. When vinpocetine was added, PDE activity was assayed in the presence of 0.2 mM $Ca^{2+}$ and 15 nM calmodulin. Control activity was 1.66±0.14 pmol/min/$10^6$ cells (mean±S.E.M.; n=8) in the absence and 4.80±0.42 pmol/min/$10^6$ cells (mean±S.E.M.; n=10) in the presence of $Ca^{2+}$ and calmodulin.

Figure 10:
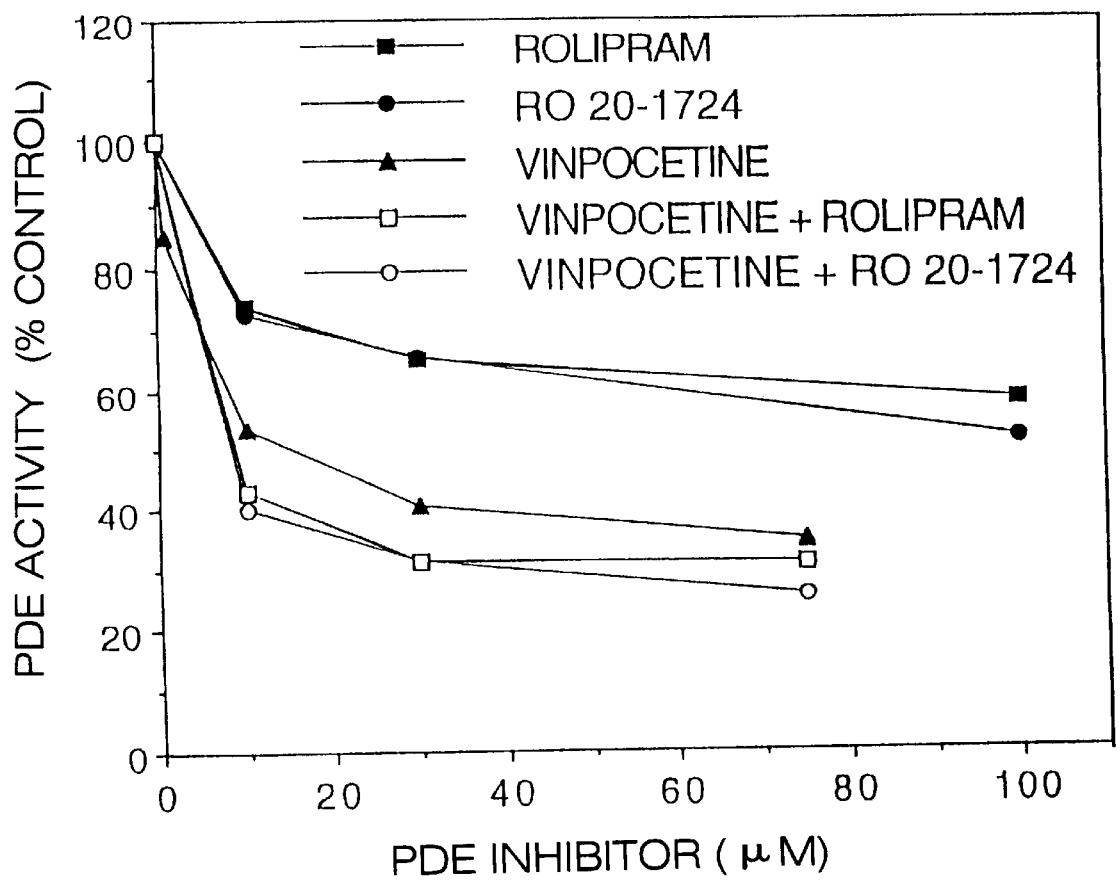
FIG. 10 is a graph showing PDE activity sensitivity to the inhibitors of FIG. 5.

As seen in FIG. 10, these inhibitors significantly inhibited PDE activity in RPMI cells at the concentrations at which they produced apoptosis. PDE inhibition appeared to plateau at ≈60% with PDE1 and ≈40% with PDE4 inhibitors; however, when added together, the effects of these inhibitors were not completely additive, suggesting that an additional form(s) of PDE may account for some of the activity in these cells. Treatment of other cell lines, which by RT-PCR were shown to express PDE1B1 mRNA: RPMI 1788, Daudi, Molt 4, NA, and Jurkat, as well as a human T lymphoma cell line, JB, with 100 μM vinpocetine induced apoptosis in every one of these cell types.

Detection of Apoptosis by Analysis of DNA Fragmentation

Cells ($10^6$) were collected by centrifugation at 670×g for 5 min. The cell pellets were rinsed once with 0.2M dibasic sodium phosphate and lysed in 300 μl of lysis buffer (50 mM Tris/HCl pH 7.5, 10 mM EDTA, 1% V/V Triton X-100) for 20 min on ice. Proteinase K was added to 0.5 mg/ml and DNase-free RNase was added to 50 μg/ml and the extract incubated at 37° C. for 1 hr. DNA was then extracted in phenol/chloroform (1:1) and chloroform (1:1) and precipitated in 2.5 volumes of ethanol. The extracted DNA was electrophoresed on 2% agarose gels, the gels stained with 0.5 μg/ml ethidium bromide and photographed under UV light.

Induction of Apoptosis in RPMI 8392 Cells by Antisense to PDE1B1

Experiments were conducted to determine if inhibition of the expression of the gene for PDE1B1 could induce apoptosis. Based on the nt sequence obtained for PDE1B1 from RPMI 8392 cells (FIG. 8), an 18 nt phosphorothioate antisense oligodeoxynucleotide (PS ODN) was synthesized, starting from 6 nt to the 5'-end of the translation initiation codon and extending over the first 4 codons of the ORF. As a control, a nonsense oligodeoxynucleotide (NS ODN) containing the same base composition, but in a random, scrambled order, was also synthesized. These synthetic phosphorothioate ODNs were added to RPMI 8392 cells in concentrations from 0.3–30 $\mu$M, and the cells were examined for apoptosis.

DNA isolated from RPMI 8392 cells was analyzed for fragmentation on 2% agarose gels after the cells were cultured with different concentrations of phosphorothioate antisense (AS) or phosphorothioate nonsense (NS) ODN for 2 days (FIG. 2A) or 1, 2 and 3 days (FIG. 2B), as indicated. Cell culture was done at a concentration of about $10^6$/ml in 1 ml volumes in 24 well plates, in RPMI 1640 growth medium, except that the fetal calf serum was heat inactivated at 65° C. for 1 hr to help minimize nuclease activity. The sequence of the 18 nt AS ODN used was 5'-GGACAGCTCCATGCTCAG-3' (SEQ. ID NO:5), and the sequence of the 18 nt NS ODN used was 5'-TACGTGAGGCACCTACGC-3' (SEQ. ID NO:6). Controls (lanes 2 in all gels) represent no additions of ODN to the cells. Markers (lanes 1 in all gels) are Hae III digests of $\phi$X174 DNA from GIBCO/BRL.

As shown in FIG. 2, 48 hr treatment with 30 $\mu$M AS ODN clearly induced apoptosis in these cells, whereas 30 $\mu$M NS ODN did not. When cells were examined for apoptosis at 1, 2, and 3 days after addition of AS and NS ODNs, it was found that after 3 days, AS ODN induced apoptosis at both 10 $\mu$M and 30 $\mu$M, whereas in all cases, NS ODN had no effect.

Effect of Antisense on Expression of PDE1B1 mRNA and Enzymatic Activity

Using quantitative RT-PCR, the effect of AS ODN and NS ODN on the level of mRNA for PDE1B1 in RPMI 8392 cells was examined. Quantitative RT-PCR was used to determine the relative amounts of $\beta$-actin and PDE1B1 mRNAs present in RPMI 8392 cells after 1 and 2 days in culture with 10 $\mu$M and 30 $\mu$M AS ODN (AS) and NS ODN (NS). Total RNA (2 $\mu$g) isolated from RPMI 8392 cells was reversed transcribed and amplified by PCR as described hereinbefore in connection with FIG. 9, except that the RT reactions for amplification of PDE1B1 and $\beta$-actin were done in separate tubes. PCR amplification was carried out for 19 cycles at 94° C. for 1 min, 58° C. for 1 min, and 72° C. for 1 min. The AS and NS ODNs used are those given in FIG. 2. Positions for PCR products PDE1B1 (CaM-PDE) and $\beta$-actin are indicated. Control (lanes 2 in both gels) represents no additions of ODN.

Markers (lane 1 in both gels) are 1 kb DNA ladder size markers from GIBCO/BRL.

As seen in FIG. 3, the level of mRNA for PDE1B1 is diminished, relative to control, 1 day after treating cells with 10 $\mu$M and 30 $\mu$M AS ODN, and absent after 2 days. The levels of $\beta$-actin mRNA, measured as a control, were unaltered by AS ODN. NS ODN had no effect on the mRNA levels of either PDE1B1 or $\beta$-actin.

RPMI 8392 cells were grown and treated with AS and NS ODN as described in the legend to FIG. 2. Cells were then collected at daily intervals and assayed for PDE activity as described in FIG. 10. Results represent the mean±the range of duplicate determinations. Control activities (pmol/min/ $10^6$ cells) were 1.17, 1.34, and 1.50 in the absence, and 3.83, 4.34, and 3.79 in the presence of $Ca^{2+}$ and calmodulin at days 1, 2, and 3, respectively.

As seen in FIG. 4, CaM-stimulated PDE activity was undetectable after 3 days in culture with 10 $\mu$M and 30 $\mu$M AS ODN, but was relatively unchanged by NS ODN. These results show that AS ODN targeted against PDE1B1 leads to a reduction in the expression of the mRNA and protein for PDE1B1 in a sequence specific manner.

Induction of PDE1B1, PDE4A and PDE4D in Mitogen-Stimulated HPBL

Figure 11A:
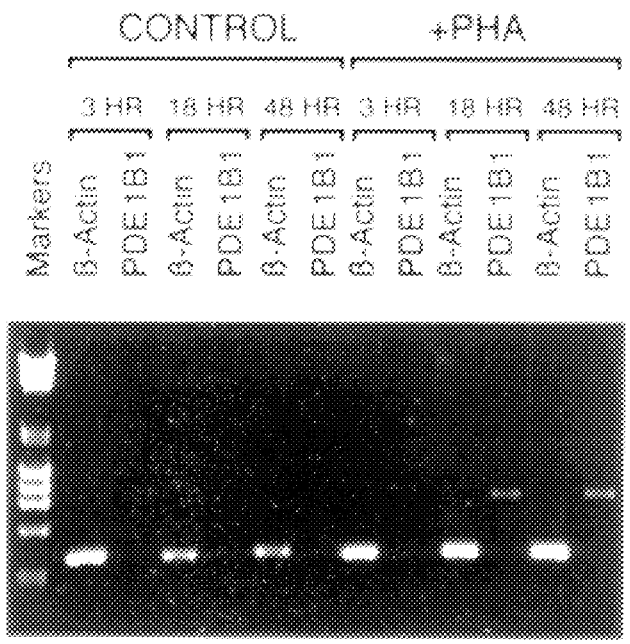
Figure 11B:
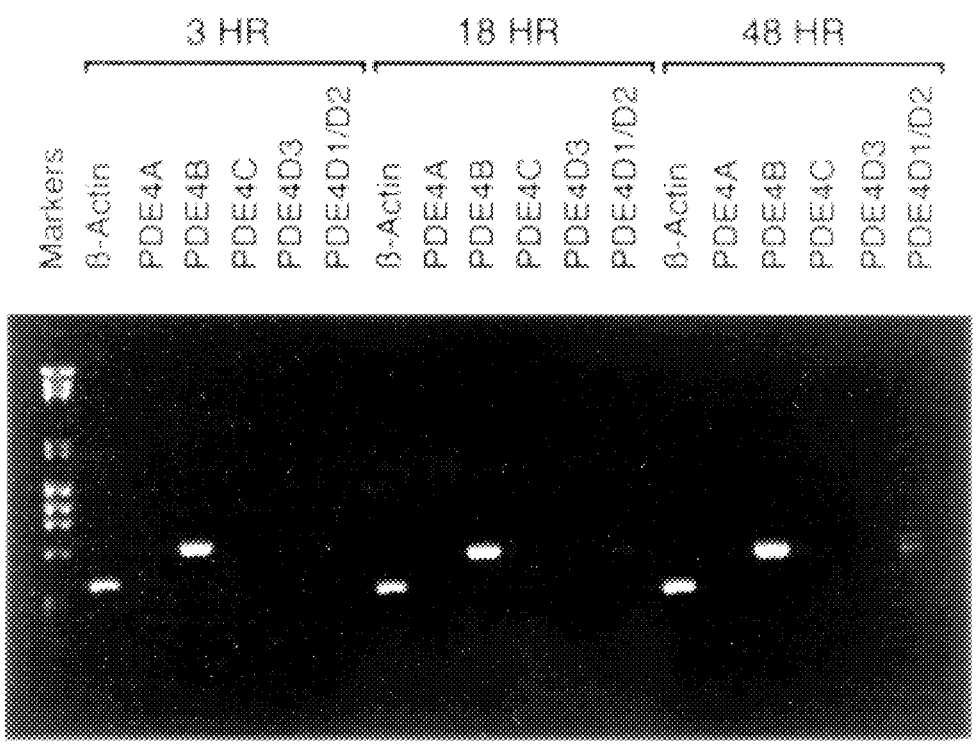

We showed previously that the mRNA for PDE1B1 is induced in HPBL following 72 hr. incubation of HPBL with PHA. Using RT-PCR with primers specific both for PDE1B1 and the four homologous genes for PDE4 (A–D), we examined the effects of 3, 18 and 48 hr. incubation of HPBL with PHA on the expression of the mRNAs for these PDEs. HPBL isolated from normal human donors were placed in culture with (+PHA) or without (CONTROL) 10 $\mu$g/ml PHA-P for the times indicated. Following incubation, RNA was prepared, reverse transcribed into cDNA, and amplified using primers specific for PDE1B1, PDE4A, 4B, 4C, 4D1, 4D2, 4D3, and $\beta$-actin, as indicated. Portions of the amplified DNA were resolved on a 1.5% agarose gel and visualized with ethidium bromide under UV light. Amplified product sizes were PDE1B1 (854 nt), PDE4A (907 nt), 4B (625 nt), 4D1 (623 nt), 4D2 (537 nt), 4D3 (623 nt), and $\beta$-actin (396 nt). DNA molecular mass markers consisting of a mixture of Lamda DNA-Hind III digests and $\phi$X 174 DNA-HAE III digests from GIBCO/BRL were run in the far left lane of the gel depicted in FIGS. 11A–11C. Isolated, quiescent HPBL does not express the mRNA for PDE1B1 (FIG. 11A Control). However, after stimulation of HPBL with PHA, expression of the mRNA for PDE1B1 is readily apparent at 18 and 48 hr. (FIG. 11A). RNA from the same cells was also reverse-transcribed and examined for the presence of mRNA transcripts for the four different PDE4 genotypes. Isolated HPBL express PDE4B as the predominant subtype, with some very small expression of PDE4D1 and D2, and a trace amount of PDE4A, as well, when analyzed for 35 cycles of PCR (FIG. 11B). Expression of PDE4C and PDE4D3 are not discernable in HPBL under these conditions. Following stimulation with PHA, there is a striking induction of PDE4A, which first becomes visible at 18 hr., and remains quite pronounced at 48 hr. (FIG. 11C). There is also some increase in the expression of PDE D1 and D2 at 18 and 48 hr., and a huge induction of PDE4D3. The induction of PDE4D3 appears to occur later than that of PDE4A, since PDE4D3 is much more prominent at 48 hr. than at 18 hr.

cAMP Induction of PDE1B1, PDE4A and PDE4D in HPBL

Since PDE4 has been shown to be induced by cAMP in a number of systems, we examined the effects of dbcAMP in combination with the PDE inhibitor, IBMX, on expression of the mRNAs for the four isogenes of PDE4 in HPBL. Conditions were the same as those set forth for FIG. 11 except that HPBL were incubated with dbcAMP (1 mM)+ IBMX (0.1 mM) for 3 or 18 hr. as indicated in part A; with 10 $\mu$/ml PHA-P for 18 hr., lanes 1 and 2, part B; or with dbcAMP (1 mM)+IBMX (0.1 mM) for 3 hr., lanes 3 and 4, part B, or 18 hr., lane 5, part B. RT-PCR amplification of transcripts for the different PDE subtypes or $\beta$-actin were then performed. As seen in FIG. 12, dbcAMP plus IBMX mimicked the effects of PHA on PDE4 expression in HPBL. After 3 hr. treatment with these cAMP-elevating agents, there was a clear induction of PDE4A, which remained fully induced at 18 hr. There was also some increase in expression of PDE4D1 and D2 and a clear induction of PDE4D3. The induction of PDE4D3 again appeared to take longer than that of PDE4A; while some expression was seen for PDE4D3 after 3 hr. treatment with these cAMP-elevating agents, expression of PDE4D3 at 18 hr. post-treatment was even greater (FIG. 12A). The same effects on PDE4 mRNA expression were observed with either dbcAMP (1 mM) or IBMX (0.1 mM) alone (data not shown).

We also investigated whether cAMP would have any effect on the expression of the mRNA for PDE1B1. As shown in FIG. 12B, dbcAMP plus IBMX also induced PDE1B1 mRNA expression in HPBL at both 3 and 18 hr. to levels comparable to that induced by PHA.

Figure 13:
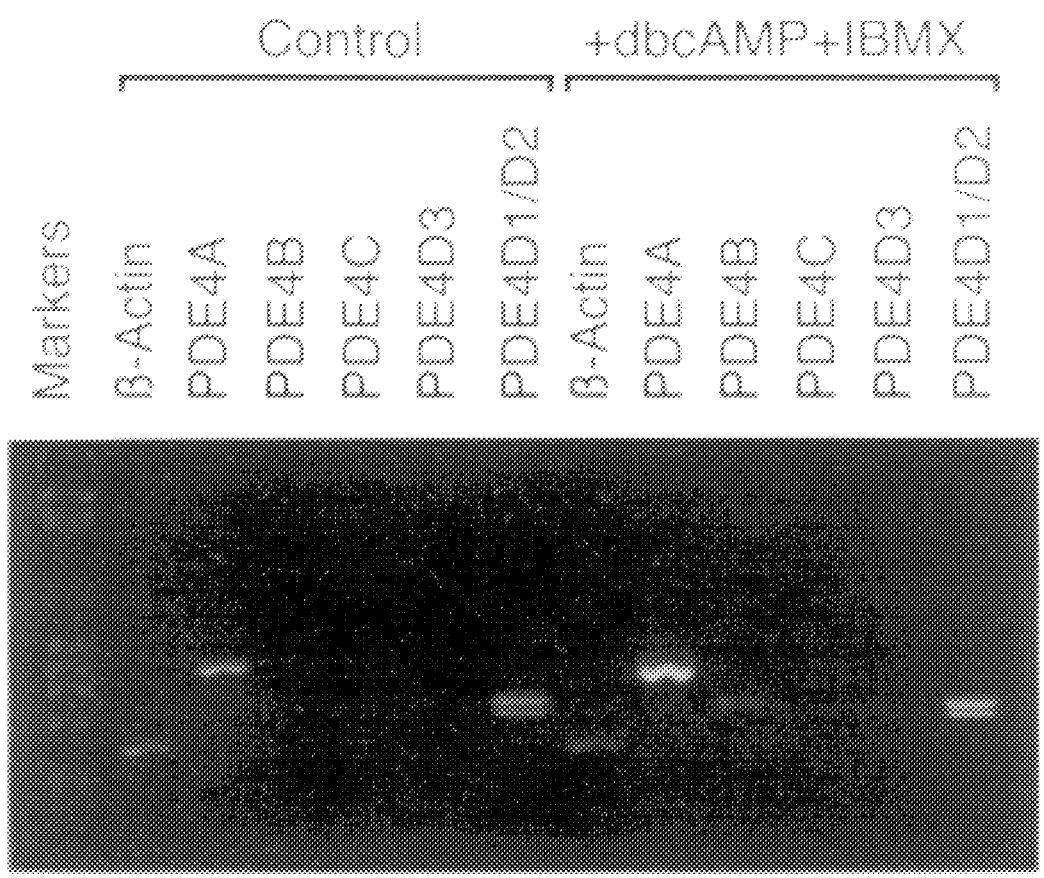
FIG. 13 is a photograph of a gel showing RT-PCR amplification of transcripts for different PDE4 subtypes in Molt 4 cells.

PDE4 Isogenes in Human T and B Leukemic Cell Lines and Effect of cAMP on This Expression Isolated, quiescent HPBL express PDE4B as the principal forms, but after mitogenic stimulation, PDE4A, and later PDE4D3 become induced. We then determined the pattern of expression of the isogenes for PDE4 in growing, transformed T and B leukemic cell lines. Molt 4 cells were cultured for 3 hr. with (+dbcAMP+IBMX) or without (Control) dbcAMP (1 mM)+IBMX (0.1 mM). Following incubation, RNA from the Molt 4 cells was reversed transcribed and cDNA for specific subtypes of PDE4 and for β-actin was amplified using specific primer pairs. Product sizes and other conditions were as described in connection with FIG. 11. As seen in FIG. 13, Molt 4, a T leukemic cell line, already shows high expression of PDE4A and PDE4D1/D2, but little expression of PDE4B, PDE4C and PDE4D3. Following incubation of these cells for 3 hr. with dbcAMP and IBMX, the expression of PDE4A is further increased, and there is a clear induction of PDE4B.

The pattern of expression of the B lymphoblastoid cell line, RPMI 8392, established from a patient with acute lymphocytic leukemia, is shown in FIG. 14. RPMI 8392 cells were cultured for 3 hr. with (+dbcAMP+IBMX) or without (Control) dbcAMP (1 mM)+IBMX (0.1 mM). Following incubation, RNA from the RPMI 8392 cells was reversed transcribed and cDNA for specific subtypes of PDE4 and for β-actin was amplified using specific primer pairs. PCR amplification was for 30 cycles in Part A and for 40 cycles in Part B. Product sizes and other conditions were as described in connection with FIG. 11. As seen for Molt cells, and in contrast to isolated, quiescent HPBL, PDE4A is already expressed at high levels in these actively growing cells, evident even at 30 cycles of PCR (FIG. 14A). Under these conditions, some expression of PDE4B is also seen (FIG. 14A), but expression of PDE4C and PDE4D3 is not detectable at the 30 cycle PCR level (not shown). Following 3 hr. treatment with dbcAMP and IBMX, there is a clear increase in the expression of PDE4B (FIG. 14A). Expression of PDE4C is apparent at 40 cycles of PCR (FIG. 14B), indicating that PDE4C is expressed in these cells, although at low levels. dbcAMP and IBMX appear to have no effect on PDE4C expression. Only a very small amount of expression of PDE4D3 is seen in these cells, even at 40 cycle PCR, but following 3 hr. treatment with dbcAMP and IBMX, expression of PDE4D3 is greatly increased. The effects of the dbcAMP plus IBMX on PDE4B and PDE4D3 in these cells is reproduced by either dbcAMP or IBMX alone (data not shown). Also, as with Molt 4 cells, PDE4D1/D2 appear to be constituitively expressed in these cells, with or without treatment with dbcAMP and IBMX (now shown).

While preferred embodiments have been shown and described, various modifications and substitutions may be made thereto without departing from the spirit and scope of the invention. Accordingly, it is to be understood that the present invention has been described by way of illustration and not limitation.

---

I claim:

1. A method of inducing programmed cell death in a cancer cell comprising:
   1) identifying the phosphodiesterase PDE1B1 in a cell line comprising said cancer cell;
   2) synthesizing an antisense oligodeoxynucleotide (AS ODN) inhibitor which binds to mRNA enconding PDE1B1; and
   3) applying the AS ODN to the cell line to inhibit enzymatic activity of said PDE1B1 and induce apoptosis within said cell.

2. The method of claim 1 wherein the AS ODN is a phosphorothioate AS ODN.

3. The method of claim 1 wherein the phosphodiesterase is identified by reverse transcription-polymerase chain reaction.

4. The method of claim 1 wherein the AS ODN has the sequence of a portion of a cDNA of said PDE1B1.

5. The method of claim 1 wherein the cell is a leukemic cell.

6. A purified and isolated polynucleotide encoding a 63 kDa calmodulin-dependent phosphodiesterase PDE1B1 of a human leukemic lymphoblastoid cell line.

7. A cDNA according to claim 6.

8. An antisense oligodeoxynucleotide (AS ODN) which binds to an mRNA encoding phosphodiesterase PDE1B1.

9. The method of claim 2 wherein the PS ODN has a sequence 5'-GGACAGCTCCATGCTCAG-3' SEQ. ID NO: 5.

* * * * *

UNITED STATES PATENT AND TRADEMARK OFFICE
CERTIFICATE OF CORRECTION

PATENT NO. : 5,885,834  
APPLICATION NO. : 08/940332  
DATED : March 23, 1999  
INVENTOR(S) : Epstein Page 1 of 1

It is certified that error appears in the above-identified patent and that said Letters Patent is hereby corrected as shown below:

<u>Column 31</u>:

Line 37 claim 1, delete "enconding" and substitute --encoding--.

Signed and Sealed this

Third Day of June, 2008

JON W. DUDAS  
*Director of the United States Patent and Trademark Office*

SEQUENCE LISTING ( 1 ) GENERAL INFORMATION:

( i i i ) NUMBER OF SEQUENCES: 7

( 2 ) INFORMATION FOR SEQ ID NO:1:

( i ) SEQUENCE CHARACTERISTICS:
        ( A ) LENGTH: 2265 base pairs
        ( B ) TYPE: nucleic acid
        ( C ) STRANDEDNESS: single
        ( D ) TOPOLOGY: linear ( i i ) MOLECULE TYPE: cDNA ( i x ) FEATURE:
        ( A ) NAME/KEY: CDS
        ( B ) LOCATION: 35..1642

( x i ) SEQUENCE DESCRIPTION: SEQ ID NO:1:

```
GCTRGTCCMY  GCCAGCCGCA  GACCGTGGCT  GAGC ATG GAG CTG TCC CCC CGC              52
                                         Met Glu Leu Ser Pro Arg
                                         1               5

AGT CCT CCG GAG ATG CTG GAG GAG TCG GAT TGC CCG TCA CCC CTG GAG             100
Ser Pro Pro Glu Met Leu Glu Glu Ser Asp Cys Pro Ser Pro Leu Glu
            10                  15                  20

CTG AAG TCA GCC CCC AGC AAG AAG ATG TGG ATT AAG CTT CGG TCT CTG             148
Leu Lys Ser Ala Pro Ser Lys Lys Met Trp Ile Lys Leu Arg Ser Leu
```

```
                    25                              30                              35
CTG  CGC  TAC  ATG  GTG  AAG  CAG  TTG  GAG  AAT  GGG  GAG  ATA  AAC  ATT  GAG       196
Leu  Arg  Tyr  Met  Val  Lys  Gln  Leu  Glu  Asn  Gly  Glu  Ile  Asn  Ile  Glu
     40                       45                      50

GAG  CTG  AAG  AAA  AAT  CTG  GAG  TAC  ACA  GCT  TCT  CTG  CTG  GAA  GCC  GTC       244
Glu  Leu  Lys  Lys  Asn  Leu  Glu  Tyr  Thr  Ala  Ser  Leu  Leu  Glu  Ala  Val
55                       60                      65                           70

TAC  ATA  GAT  GAG  ACA  CGG  CAA  ATC  TTG  GAC  ACG  GAG  GAC  GAG  CTG  CAG       292
Tyr  Ile  Asp  Glu  Thr  Arg  Gln  Ile  Leu  Asp  Thr  Glu  Asp  Glu  Leu  Gln
                    75                      80                           85

GAG  CTG  CGG  TCA  GAT  GCC  GTG  CCT  TCA  GAG  GTG  CGG  GAC  TGG  CTG  GCC       340
Glu  Leu  Arg  Ser  Asp  Ala  Val  Pro  Ser  Glu  Val  Arg  Asp  Trp  Leu  Ala
               90                      95                          100

TCC  ACC  TTC  ACC  CAG  CAG  GCC  CGG  GCC  AAA  GGC  CGC  CGA  GCA  GAG  GAG       388
Ser  Thr  Phe  Thr  Gln  Gln  Ala  Arg  Ala  Lys  Gly  Arg  Arg  Ala  Glu  Glu
          105                          110                     115

AAG  CCC  AAG  TTC  CGA  AGC  ATT  GTG  CAC  GCT  GTG  CAG  GCT  GGG  ATC  TTC       436
Lys  Pro  Lys  Phe  Arg  Ser  Ile  Val  His  Ala  Val  Gln  Ala  Gly  Ile  Phe
     120                          125                          130

GTG  GAA  CGG  ATG  TTC  CGG  AGA  ACA  TAC  ACC  TCT  GTG  GGC  CCC  ACT  TAC       484
Val  Glu  Arg  Met  Phe  Arg  Arg  Thr  Tyr  Thr  Ser  Val  Gly  Pro  Thr  Tyr
135                      140                     145                          150

TCT  ACT  GCG  GTT  CTC  AAC  TGT  CTC  AAG  AAC  TTG  GAT  CTC  TGG  TGC  TTT       532
Ser  Thr  Ala  Val  Leu  Asn  Cys  Leu  Lys  Asn  Leu  Asp  Leu  Trp  Cys  Phe
                    155                     160                          165

GAT  GTC  TTT  TCC  TTG  AAC  CAG  GCA  GCA  GAT  GAC  CAT  GCC  CTG  AGG  ACC       580
Asp  Val  Phe  Ser  Leu  Asn  Gln  Ala  Ala  Asp  Asp  His  Ala  Leu  Arg  Thr
               170                          175                     180

ATT  GTT  TTT  GAG  TTG  CTG  ACT  CGG  CAT  AAC  CTC  ATC  AGC  CGC  TTC  AAG       628
Ile  Val  Phe  Glu  Leu  Leu  Thr  Arg  His  Asn  Leu  Ile  Ser  Arg  Phe  Lys
          185                          190                     195

ATT  CCC  ACT  GTG  TTT  TTG  ATG  AGT  TTC  CTG  GAT  GCC  TTG  GAG  ACA  GGC       676
Ile  Pro  Thr  Val  Phe  Leu  Met  Ser  Phe  Leu  Asp  Ala  Leu  Glu  Thr  Gly
     200                          205                          210

TAT  GGG  AAG  TAC  AAG  AAT  CCT  TAC  CAC  AAC  CAG  ATC  CAC  GCA  GCC  GAT       724
Tyr  Gly  Lys  Tyr  Lys  Asn  Pro  Tyr  His  Asn  Gln  Ile  His  Ala  Ala  Asp
215                      220                          225                     230

GTT  ACC  CAG  ACA  GTC  CAT  TGC  TTC  TTG  CTC  CGC  ACA  GGG  ATG  GTG  CAC       772
Val  Thr  Gln  Thr  Val  His  Cys  Phe  Leu  Leu  Arg  Thr  Gly  Met  Val  His
                    235                     240                          245

TGC  CTG  TCG  GAG  ATT  GAG  CTC  CTG  GCC  ATC  ATC  TTT  GCT  GCA  GCT  ATC       820
Cys  Leu  Ser  Glu  Ile  Glu  Leu  Leu  Ala  Ile  Ile  Phe  Ala  Ala  Ala  Ile
               250                          255                     260

CAT  GAT  TAT  GAG  CAC  ACG  GGC  ACT  ACC  AAC  AGC  TTC  CAC  ATC  CAG  ACC       868
His  Asp  Tyr  Glu  His  Thr  Gly  Thr  Thr  Asn  Ser  Phe  His  Ile  Gln  Thr
          265                          270                     275

AAG  TCA  GAA  TGT  GCC  ATC  GTG  TAC  AAT  GAT  CGT  TCA  GTG  CTG  GAG  AAT       916
Lys  Ser  Glu  Cys  Ala  Ile  Val  Tyr  Asn  Asp  Arg  Ser  Val  Leu  Glu  Asn
     280                          285                          290

CAC  CAC  ATC  AGC  TCT  GTT  TTC  CGA  TTG  ATG  CAG  GAT  GAT  GAG  ATG  AAC       964
His  His  Ile  Ser  Ser  Val  Phe  Arg  Leu  Met  Gln  Asp  Asp  Glu  Met  Asn
295                      300                          305                     310

ATT  TTC  ATC  AAC  CTC  ACC  AAG  GAT  GAG  TTT  GTA  GAA  CTC  CGA  GCC  CTG      1012
Ile  Phe  Ile  Asn  Leu  Thr  Lys  Asp  Glu  Phe  Val  Glu  Leu  Arg  Ala  Leu
                    315                     320                          325

GTC  ATT  GAG  ATG  GTG  TTG  GCC  ACA  GAC  ATG  TCC  TGC  CAT  TTC  CAG  CAA      1060
Val  Ile  Glu  Met  Val  Leu  Ala  Thr  Asp  Met  Ser  Cys  His  Phe  Gln  Gln
               330                          335                     340

GTG  AAG  ACC  ATG  AAG  ACA  GCC  TTG  CAA  CAG  CTG  GAG  AGG  ATT  GAC  AAG      1108
Val  Lys  Thr  Met  Lys  Thr  Ala  Leu  Gln  Gln  Leu  Glu  Arg  Ile  Asp  Lys
```

-continued

```
                          345                         350                             355
CCC  AAG  GCC  CTG  TCT  CTA  CTG  CTC  CAT  GCT  GCT  GAC  ATC  AGC  CAC  CCA                1156
Pro  Lys  Ala  Leu  Ser  Leu  Leu  Leu  His  Ala  Ala  Asp  Ile  Ser  His  Pro
     360                      365                         370

ACC  AAG  CAG  TGG  TTG  GTC  CAC  AGC  CGT  TGG  ACC  AAG  GCC  CTC  ATG  GAG                1204
Thr  Lys  Gln  Trp  Leu  Val  His  Ser  Arg  Trp  Thr  Lys  Ala  Leu  Met  Glu
375                           380                        385                      390

GAA  TTC  TTC  CGT  CAG  GGT  GAC  AAG  GAG  GCA  GAG  TTG  GGC  CTG  CCC  TTT                1252
Glu  Phe  Phe  Arg  Gln  Gly  Asp  Lys  Glu  Ala  Glu  Leu  Gly  Leu  Pro  Phe
                    395                      400                           405

TCT  CCA  CTC  TGT  GAC  CGC  ACT  TCC  ACT  CTA  GTG  GCA  CAG  TCT  CAG  ATA                1300
Ser  Pro  Leu  Cys  Asp  Arg  Thr  Ser  Thr  Leu  Val  Ala  Gln  Ser  Gln  Ile
               410                           415                      420

GGG  TTC  ATC  GAC  TTC  ATT  GTG  GAG  CCC  ACA  TTC  TCT  GTG  CTG  ACT  GAC                1348
Gly  Phe  Ile  Asp  Phe  Ile  Val  Glu  Pro  Thr  Phe  Ser  Val  Leu  Thr  Asp
          425                           430                           435

GTG  GCA  GAG  AAG  AGT  GTT  CAG  CCC  CTG  GCG  GAT  GAG  GAC  TCC  AAG  TCT                1396
Val  Ala  Glu  Lys  Ser  Val  Gln  Pro  Leu  Ala  Asp  Glu  Asp  Ser  Lys  Ser
     440                      445                          450

AAA  AAC  CAG  CCC  AGC  TTT  CAG  TGG  CGC  CAG  CCC  TCT  CTG  GAT  GTG  GAA                1444
Lys  Asn  Gln  Pro  Ser  Phe  Gln  Trp  Arg  Gln  Pro  Ser  Leu  Asp  Val  Glu
455                           460                        465                      470

GTG  GGA  GAC  CCC  AAC  CCT  GAT  GTG  GTC  AGC  TTT  CGT  TCC  ACC  TGG  GTC                1492
Val  Gly  Asp  Pro  Asn  Pro  Asp  Val  Val  Ser  Phe  Arg  Ser  Thr  Trp  Val
                    475                      480                           485

AAG  CGC  ATT  CAG  GAG  AAC  AAG  CAG  AAA  TGG  AAG  GAA  CGG  GCA  GCA  AGT                1540
Lys  Arg  Ile  Gln  Glu  Asn  Lys  Gln  Lys  Trp  Lys  Glu  Arg  Ala  Ala  Ser
               490                           495                      500

GGC  ATC  ACC  AAC  CAG  ATG  TCC  ATT  GAC  GAG  CTG  TCC  CCC  TGT  GAA  GAA                1588
Gly  Ile  Thr  Asn  Gln  Met  Ser  Ile  Asp  Glu  Leu  Ser  Pro  Cys  Glu  Glu
          505                           510                           515

GAG  GCC  CCC  CCA  TCC  CCT  GCC  GAA  GAT  GAA  CAC  AAC  CAG  AAT  GGG  AAT                1636
Glu  Ala  Pro  Pro  Ser  Pro  Ala  Glu  Asp  Glu  His  Asn  Gln  Asn  Gly  Asn
     520                      525                          530

CTG  GAT       TAGCCCTGGG  GCTGGCCCAG  GTCTTCATTG  AGTCCAAAGT  GTTTGATGTC                      1692
Leu  Asp
535

ATCAGCACCA  TCCATCAGGA  CTGGCTCCCC  CATCTGCTCC  AAGGGAGCGT  GGTCGTGGAA                          1752

GAAACAACCC  ACCTGAAGGC  CAAATGCCAG  AGATTTGGGG  TTGGGGAAAG  GGCCCCTCCC                          1812

CACCTGACAC  CCACTGGGGT  GCACTTTAAT  GTTCCGGCAG  CAAGACTGGG  GAACTTCAGG                          1872

CTCCCAGTGG  TCACTGTGCC  CATCCCTCAG  CCTCTGGATT  CTCTTCATGG  CCAGGTGGCT                          1932

GCCAGGGAGC  GGGGAGCTTC  CTGGAGGCTT  CCCAGGGCCT  TGGGGAAGGG  TCAGAGATGC                          1992

CAGCCCCCTG  GGACCTCCCC  CATCCTTTTT  GCCTCCAAGT  TTCTAAGCAA  TACATTTTGG                          2052

GGGTTCCCTC  AGCCCCCCAC  CCCAGATCTT  AGCTGGCAGG  TCTGGGTGCC  CCTTTTCCTC                          2112

CCCTGGGAAG  GGCTGGAATA  GGATAGAAAG  CTGGGGGTTT  TCAGAGCCCT  ATGTGTGGGG                          2172

AGGGGAGTGG  ATTCCTTCAG  GGCATGGTAC  CTTTCTAGGA  TCTGGGAATG  GGGTGGAGAG                          2232

GACATCCTCT  TCACCCCAGA  ATTGCGGGAA  TTC                                                         2265
```

( 2 ) INFORMATION FOR SEQ ID NO:2:

( i ) SEQUENCE CHARACTERISTICS:
        ( A ) LENGTH: 536 amino acids
        ( B ) TYPE: amino acid
        ( D ) TOPOLOGY: linear ( i i ) MOLECULE TYPE: protein ( x i ) SEQUENCE DESCRIPTION: SEQ ID NO:2:

| Met | Glu | Leu | Ser | Pro | Arg | Ser | Pro | Pro | Glu | Met | Leu | Glu | Ser | Asp |
|-----|-----|-----|-----|-----|-----|-----|-----|-----|-----|-----|-----|-----|-----|-----|
| 1   |     |     |     | 5   |     |     |     |     | 10  |     |     |     |     | 15  |

| Cys | Pro | Ser | Pro | Leu | Glu | Leu | Lys | Ser | Ala | Pro | Ser | Lys | Met | Trp |
|-----|-----|-----|-----|-----|-----|-----|-----|-----|-----|-----|-----|-----|-----|-----|
|     |     |     | 20  |     |     |     | 25  |     |     |     |     | 30  |     |     |

| Ile | Lys | Leu | Arg | Ser | Leu | Leu | Arg | Tyr | Met | Val | Lys | Gln | Leu | Glu | Asn |
|-----|-----|-----|-----|-----|-----|-----|-----|-----|-----|-----|-----|-----|-----|-----|-----|
|     |     |     | 35  |     |     |     | 40  |     |     |     |     | 45  |     |     |     |

| Gly | Glu | Ile | Asn | Ile | Glu | Glu | Leu | Lys | Lys | Asn | Leu | Glu | Tyr | Thr | Ala |
|-----|-----|-----|-----|-----|-----|-----|-----|-----|-----|-----|-----|-----|-----|-----|-----|
|     | 50  |     |     |     |     | 55  |     |     |     |     | 60  |     |     |     |     |

| Ser | Leu | Leu | Glu | Ala | Val | Tyr | Ile | Asp | Glu | Thr | Arg | Gln | Ile | Leu | Asp |
|-----|-----|-----|-----|-----|-----|-----|-----|-----|-----|-----|-----|-----|-----|-----|-----|
| 65  |     |     |     |     | 70  |     |     |     |     | 75  |     |     |     |     | 80  |

| Thr | Glu | Asp | Glu | Leu | Gln | Glu | Leu | Arg | Ser | Asp | Ala | Val | Pro | Ser | Glu |
|-----|-----|-----|-----|-----|-----|-----|-----|-----|-----|-----|-----|-----|-----|-----|-----|
|     |     |     |     | 85  |     |     |     |     | 90  |     |     |     |     | 95  |     |

| Val | Arg | Asp | Trp | Leu | Ala | Ser | Thr | Phe | Thr | Gln | Gln | Ala | Arg | Ala | Lys |
|-----|-----|-----|-----|-----|-----|-----|-----|-----|-----|-----|-----|-----|-----|-----|-----|
|     |     |     | 100 |     |     |     |     | 105 |     |     |     |     | 110 |     |     |

| Gly | Arg | Arg | Ala | Glu | Glu | Lys | Pro | Lys | Phe | Arg | Ser | Ile | Val | His | Ala |
|-----|-----|-----|-----|-----|-----|-----|-----|-----|-----|-----|-----|-----|-----|-----|-----|
|     |     | 115 |     |     |     |     | 120 |     |     |     |     | 125 |     |     |     |

| Val | Gln | Ala | Gly | Ile | Phe | Val | Glu | Arg | Met | Phe | Arg | Arg | Thr | Tyr | Thr |
|-----|-----|-----|-----|-----|-----|-----|-----|-----|-----|-----|-----|-----|-----|-----|-----|
|     | 130 |     |     |     |     | 135 |     |     |     |     | 140 |     |     |     |     |

| Ser | Val | Gly | Pro | Thr | Tyr | Ser | Thr | Ala | Val | Leu | Asn | Cys | Leu | Lys | Asn |
|-----|-----|-----|-----|-----|-----|-----|-----|-----|-----|-----|-----|-----|-----|-----|-----|
| 145 |     |     |     |     | 150 |     |     |     |     | 155 |     |     |     |     | 160 |

| Leu | Asp | Leu | Trp | Cys | Phe | Asp | Val | Phe | Ser | Leu | Asn | Gln | Ala | Ala | Asp |
|-----|-----|-----|-----|-----|-----|-----|-----|-----|-----|-----|-----|-----|-----|-----|-----|
|     |     |     |     | 165 |     |     |     |     | 170 |     |     |     |     | 175 |     |

| Asp | His | Ala | Leu | Arg | Thr | Ile | Val | Phe | Glu | Leu | Leu | Thr | Arg | His | Asn |
|-----|-----|-----|-----|-----|-----|-----|-----|-----|-----|-----|-----|-----|-----|-----|-----|
|     |     |     | 180 |     |     |     |     | 185 |     |     |     |     | 190 |     |     |

| Leu | Ile | Ser | Arg | Phe | Lys | Ile | Pro | Thr | Val | Phe | Leu | Met | Ser | Phe | Leu |
|-----|-----|-----|-----|-----|-----|-----|-----|-----|-----|-----|-----|-----|-----|-----|-----|
|     |     | 195 |     |     |     |     | 200 |     |     |     |     | 205 |     |     |     |

| Asp | Ala | Leu | Glu | Thr | Gly | Tyr | Gly | Lys | Tyr | Lys | Asn | Pro | Tyr | His | Asn |
|-----|-----|-----|-----|-----|-----|-----|-----|-----|-----|-----|-----|-----|-----|-----|-----|
|     | 210 |     |     |     |     | 215 |     |     |     |     | 220 |     |     |     |     |

| Gln | Ile | His | Ala | Ala | Asp | Val | Thr | Gln | Thr | Val | His | Cys | Phe | Leu | Leu |
|-----|-----|-----|-----|-----|-----|-----|-----|-----|-----|-----|-----|-----|-----|-----|-----|
| 225 |     |     |     |     | 230 |     |     |     |     | 235 |     |     |     |     | 240 |

| Arg | Thr | Gly | Met | Val | His | Cys | Leu | Ser | Glu | Ile | Glu | Leu | Leu | Ala | Ile |
|-----|-----|-----|-----|-----|-----|-----|-----|-----|-----|-----|-----|-----|-----|-----|-----|
|     |     |     |     | 245 |     |     |     |     | 250 |     |     |     |     | 255 |     |

| Ile | Phe | Ala | Ala | Ala | Ile | His | Asp | Tyr | Glu | His | Thr | Gly | Thr | Thr | Asn |
|-----|-----|-----|-----|-----|-----|-----|-----|-----|-----|-----|-----|-----|-----|-----|-----|
|     |     |     | 260 |     |     |     |     | 265 |     |     |     |     | 270 |     |     |

| Ser | Phe | His | Ile | Gln | Thr | Lys | Ser | Glu | Cys | Ala | Ile | Val | Tyr | Asn | Asp |
|-----|-----|-----|-----|-----|-----|-----|-----|-----|-----|-----|-----|-----|-----|-----|-----|
|     |     | 275 |     |     |     |     | 280 |     |     |     |     | 285 |     |     |     |

| Arg | Ser | Val | Leu | Glu | Asn | His | His | Ile | Ser | Ser | Val | Phe | Arg | Leu | Met |
|-----|-----|-----|-----|-----|-----|-----|-----|-----|-----|-----|-----|-----|-----|-----|-----|
|     | 290 |     |     |     |     | 295 |     |     |     |     | 300 |     |     |     |     |

| Gln | Asp | Asp | Glu | Met | Asn | Ile | Phe | Ile | Asn | Leu | Thr | Lys | Asp | Glu | Phe |
|-----|-----|-----|-----|-----|-----|-----|-----|-----|-----|-----|-----|-----|-----|-----|-----|
| 305 |     |     |     |     | 310 |     |     |     |     | 315 |     |     |     |     | 320 |

| Val | Glu | Leu | Arg | Ala | Leu | Val | Ile | Glu | Met | Val | Leu | Ala | Thr | Asp | Met |
|-----|-----|-----|-----|-----|-----|-----|-----|-----|-----|-----|-----|-----|-----|-----|-----|
|     |     |     |     | 325 |     |     |     |     | 330 |     |     |     |     | 335 |     |

| Ser | Cys | His | Phe | Gln | Gln | Val | Lys | Thr | Met | Lys | Thr | Ala | Leu | Gln | Gln |
|-----|-----|-----|-----|-----|-----|-----|-----|-----|-----|-----|-----|-----|-----|-----|-----|
|     |     |     | 340 |     |     |     |     | 345 |     |     |     |     | 350 |     |     |

| Leu | Glu | Arg | Ile | Asp | Lys | Pro | Lys | Ala | Leu | Ser | Leu | Leu | Leu | His | Ala |
|-----|-----|-----|-----|-----|-----|-----|-----|-----|-----|-----|-----|-----|-----|-----|-----|
|     |     | 355 |     |     |     |     | 360 |     |     |     |     | 365 |     |     |     |

| Ala | Asp | Ile | Ser | His | Pro | Thr | Lys | Gln | Trp | Leu | Val | His | Ser | Arg | Trp |
|-----|-----|-----|-----|-----|-----|-----|-----|-----|-----|-----|-----|-----|-----|-----|-----|
|     | 370 |     |     |     |     | 375 |     |     |     |     | 380 |     |     |     |     |

| Thr | Lys | Ala | Leu | Met | Glu | Glu | Phe | Phe | Arg | Gln | Gly | Asp | Lys | Glu | Ala |
|-----|-----|-----|-----|-----|-----|-----|-----|-----|-----|-----|-----|-----|-----|-----|-----|
| 385 |     |     |     |     | 390 |     |     |     |     | 395 |     |     |     |     | 400 |

| Glu | Leu | Gly | Leu | Pro | Phe | Ser | Pro | Leu | Cys | Asp | Arg | Thr | Ser | Thr | Leu |
|-----|-----|-----|-----|-----|-----|-----|-----|-----|-----|-----|-----|-----|-----|-----|-----|
|     |     |     |     | 405 |     |     |     |     | 410 |     |     |     |     | 415 |     |

| | | | | | | | | | | | | | | |
|---|---|---|---|---|---|---|---|---|---|---|---|---|---|---|
| Val | Ala | Gln | Ser 420 | Gln | Ile | Gly | Phe | Ile 425 | Asp | Phe | Ile | Val | Glu 430 | Pro | Thr |
| Phe | Ser | Val 435 | Leu | Thr | Asp | Val | Ala 440 | Glu | Lys | Ser | Val | Gln 445 | Pro | Leu | Ala |
| Asp | Glu 450 | Asp | Ser | Lys | Ser | Asn 455 | Gln | Pro | Ser | Phe 460 | Gln | Trp | Arg | Gln | |
| Pro 465 | Ser | Leu | Asp | Val | Glu 470 | Val | Gly | Asp | Pro | Asn 475 | Pro | Asp | Val | Val | Ser 480 |
| Phe | Arg | Ser | Thr | Trp 485 | Val | Lys | Arg | Ile | Gln 490 | Glu | Asn | Lys | Gln | Lys 495 | Trp |
| Lys | Glu | Arg | Ala 500 | Ala | Ser | Gly | Ile | Thr 505 | Asn | Gln | Met | Ser | Ile 510 | Asp | Glu |
| Leu | Ser | Pro 515 | Cys | Glu | Glu | Glu | Ala 520 | Pro | Pro | Ser | Pro | Ala 525 | Glu | Asp | Glu |
| His | Asn 530 | Gln | Asn | Gly | Asn | Leu 535 | Asp | | | | | | | | |

(2) INFORMATION FOR SEQ ID NO:3:

(i) SEQUENCE CHARACTERISTICS:
        (A) LENGTH: 325 base pairs
        (B) TYPE: nucleic acid
        (C) STRANDEDNESS: single
        (D) TOPOLOGY: linear (ii) MOLECULE TYPE: mRNA (xi) SEQUENCE DESCRIPTION: SEQ ID NO:3:

```
GCCAGCCGCA GACCGUGGCU GAGCAUGGAG CUGUCCCCCC GCAGUCCUCC GGAGAUGCUG      60
GAGGAGUCGG AUUGCCCGUC ACCCCAUGGG CUGAAGUCAG CCCCCAGCAA GAAGAUGUGG     120
AUUAAGCUUC GGUCUCUGCU GCGCUACAUG GUGAAGCAGU GGAGAAUGG GGAGAUAAAC      180
AUUGAGGAGC UGAAGAAAAA UCUGGAGUAC ACAGCUUCUC UGCUGGAAGC CGUCUACAUA     240
GAUGAGACAC GGCAAAUCUU GGACACGGAG GACGAGCUGC AGGAGCUGCG GUCAGAUGCC     300
GUGCCUUCGG AGGUGCGGGA CUGGC                                          325
```

(2) INFORMATION FOR SEQ ID NO:4:

(i) SEQUENCE CHARACTERISTICS:
        (A) LENGTH: 18 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "oligonucleotide"

(xi) SEQUENCE DESCRIPTION: SEQ ID NO:4:

```
CTGAGCATGG AGCTGTCC                                                    18
```

(2) INFORMATION FOR SEQ ID NO:5:

(i) SEQUENCE CHARACTERISTICS:
        (A) LENGTH: 18 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "oligonucleotide"

(xi) SEQUENCE DESCRIPTION: SEQ ID NO:5:

```
GGACAGCTCC ATGCTCAG                                                    18
```

( 2 ) INFORMATION FOR SEQ ID NO:6:

( i ) SEQUENCE CHARACTERISTICS:
        ( A ) LENGTH: 18 base pairs
        ( B ) TYPE: nucleic acid
        ( C ) STRANDEDNESS: single
        ( D ) TOPOLOGY: linear ( i i ) MOLECULE TYPE: other nucleic acid
        ( A ) DESCRIPTION: /desc = "oligonucleotide"

( x i ) SEQUENCE DESCRIPTION: SEQ ID NO:6:

TACGTGAGGC ACCTACGC                         18

( 2 ) INFORMATION FOR SEQ ID NO:7:

( i ) SEQUENCE CHARACTERISTICS:
        ( A ) LENGTH: 18 base pairs
        ( B ) TYPE: nucleic acid
        ( C ) STRANDEDNESS: single
        ( D ) TOPOLOGY: linear ( i i ) MOLECULE TYPE: other nucleic acid
        ( A ) DESCRIPTION: /desc = "oligonucleotide"

( x i ) SEQUENCE DESCRIPTION: SEQ ID NO:7:

GTATGGCAGG ATGGCCCC                         18